US012564569B2

(12) United States Patent
Zheng

(10) Patent No.: US 12,564,569 B2
(45) Date of Patent: Mar. 3, 2026

(54) CARBOPLATIN COMPLEX AND PHARMACEUTICAL PREPARATION THEREOF

(71) Applicant: ADVANCHL BIOTECHNOLOGY SERVICE CENTER (SHANGHAI), Shanghai (CN)

(72) Inventor: Jianqiang Zheng, Beijing (CN)

(73) Assignee: ADVANCHL BIOTECHNOLOGY SERVICE CENTER (SHANGHAI), Shanghai (CN)

( * ) Notice: Subject to any disclaimer, the term of this patent is extended or adjusted under 35 U.S.C. 154(b) by 1014 days.

(21) Appl. No.: 17/681,197

(22) Filed: Feb. 25, 2022

(65) Prior Publication Data

US 2022/0175715 A1 Jun. 9, 2022

Related U.S. Application Data

(63) Continuation of application No. PCT/CN2020/111393, filed on Aug. 26, 2020.

(30) Foreign Application Priority Data

Aug. 27, 2019 (CN) ......................... 201910797724.6

(51) Int. Cl.

*A61K 31/282* (2006.01)
*A61K 9/00* (2006.01)
*A61K 9/08* (2006.01)
*A61K 47/54* (2017.01)

(52) U.S. Cl.

CPC .......... *A61K 31/282* (2013.01); *A61K 9/0019* (2013.01); *A61K 9/08* (2013.01); *A61K 47/542* (2017.08)

(58) Field of Classification Search

CPC .. A61K 31/282; A61K 47/542; A61K 9/0019; A61K 9/08

See application file for complete search history.

(56) References Cited

U.S. PATENT DOCUMENTS 6,699,901 B1 * 3/2004 Yang .................... A61K 31/282 556/137

FOREIGN PATENT DOCUMENTS

| | | | |
|---|---|---|---|
| CN | 1311183 | A | 9/2001 |
| CN | 104122280 | A | 10/2014 |
| CN | 104127402 | A | 11/2014 |
| CN | 104693245 | A | 6/2015 |
| CN | 107167482 | A | 9/2017 |
| CN | 109053808 | A | 12/2018 |
| RU | 2676269 | C1 | 12/2018 |
| WO | 2018233273 | A1 | 12/2018 |

OTHER PUBLICATIONS

Yang, X., Determination methods for the anticancer drug dicycloplatin, a supramolecule assembled through hydrogen bonding, Analyst, 140, pp. 2704-2712 (Year: 2015).*

Office Action issued on Mar. 2, 2023, in corresponding Japanese Application No. 2022-513668, 8 pages.

Office Action issued on Mar. 22, 2023, in corresponding Russian Application No. 2022107922, 14 pages.

Duggirala et al., “Pharmaceutical cocrystals: along the path to improved medicines”, Chem Commun, 2016, vol. 52, pp. 640-655.

Schultheiss et al., “Pharmaceutical Cocrystals and Their Physicochemical Properties”, American Chemical Society, Crystal Growth & Design, 2009, vol. 9, No. 6, pp. 2950-2967.

Kummerer, “Pharmaceuticals in the Environment”, Annual Review of Environment and Resources, 2010, vol. 35, pp. 57-75.

Office Action issued on Oct. 31, 2022, in corresponding Russian Application No. 2022107922, 18 pages.

Office Action issued on Nov. 16, 2022, in corresponding Chinese Application No. 202010872938.8, 14 pages.

Lu et al., “Synthesis and Characterization of Novel Ferrocenyl α-Aminophosphonic Esters”, Chinese Journal of Organic Chemistry, Department of Chemistry, Zhengzhou University, 2008, vol. 28 No. 10, pp. 1735-1739, with English abstract.

Yu, et al., “Spectral Analysis of Chemical Constituents of Natural Medicines”, 2008, ISBN 9787506739108, also published by China Medical Science and Technology Press in 1970, 3 pages with partial English translation provided.

First Office Action issued on Jun. 28, 2022, in connection with corresponding Chinese Application 202010872938.8; 17 pages (with English Translation).

Xuqing Yang et al., “Determination methods for the anticancer drug dicycloplatin, a supramolecule assembled through hydrogen bonding”, Royal Society of Chemistry, CNCNP202012462, Analyst, 2015, vol. 140, pp. 2704-2712.

International Search Report issued on Nov. 27, 2020 in corresponding International application No. PCT/CN2020/111393; 12 pages.

(Continued)

*Primary Examiner* — Adam C Milligan
*Assistant Examiner* — Ernesto Valle
(74) *Attorney, Agent, or Firm* — Maier & Maier, PLLC

(57) ABSTRACT

Provided are a carboplatin complex and a pharmaceutical preparation thereof. The carboplatin complex is a complex formed by combining carboplatin and 1,1-cyclobutanedicarboxylic acid through two hydrogen bonds, each of the two hydrogen bonds is formed between a carbonyl oxygen of a carboplatin molecule and a carboxyl hydrogen of a 1,1-cyclobutanedicarboxylic acid molecule. The present disclosure further provides use of the carboplatin complex in manufacture of an antitumor drug, an antibacterial drug, an antifungal drug, or an antiviral drug, and a quality control method for the carboplatin complex.

4 Claims, 11 Drawing Sheets

(56) References Cited

OTHER PUBLICATIONS

Title: Structural Studies of the Supramolecular Anticancer Drug Bicycloplatin, Author: Xuqing Yang, Xianglin Jin, etc., Publisher: Science China Press, Publication date: Dec. 31, 2010 URL:https://www.ixueshu.com/document/cbdda1caac6215c2a9b56fc10e6b366e318947a18e7f9386.html, 8 pgs.

* cited by examiner

CARBOPLATIN COMPLEX AND PHARMACEUTICAL PREPARATION THEREOF

CROSS-REFERENCE TO RELATED APPLICATIONS

This application is a continuation of International Application No. PCT/CN2020/111393, filed on Aug. 26, 2020, which claims priority to Chinese Patent Application No. 2019107977246, filed on Aug. 27, 2019. The disclosures of the aforementioned applications are hereby incorporated by reference in their entireties.

TECHNICAL FIELD

The present disclosure relates to a platinum derivative and particularly, to a carboplatin complex obtained by hydrogen bonding on the basis of carboplatin molecules, and further relates to a platinum-based pharmaceutical preparation obtained from the carboplatin complex.

BACKGROUND

The discovery of the antitumor efficacy of cis-dichlorodiammine platinum initiates the research and application of platinum-based anticancer drugs, and also makes the research of platinum-based anticancer drugs become one of hot spots in the field of tumor therapy in recent years. Cisplatinum (Cisplatin) containing cis-dichlorodiammine platinum as an active component is the first platinum-based anticancer drug in humans, and it is a non-cell specific drug. Research shows that the cisplatin can bind to DNA and cause cross-linking, thereby destroying the function of DNA and inhibiting DNA replication of cells. In clinical application, the cisplatin has a broad antitumor spectrum and has been applied to head and neck squamous cell carcinoma, ovarian cancer, embryonal carcinoma, seminoma, lung cancer, thyroid cancer, lymphatic sarcoma, reticulum cell sarcoma and so on. Big data statistics show that cisplatin has a good effect of tumor treatment, but it also shows serious toxic and side effects in clinical practice. On the other hand, considering the drug resistance of chemotherapy drugs, there is still a need for finding alternative drugs.

Carboplatin is a second-generation platinum-based anticancer drug obtained by molecular modification of cisplatin, and is a novel platinum compound obtained by simultaneously replacing two chlorine atoms in the cisplatin molecule with 1,1-cyclobutanedicarboxylic acid. It partially overcomes the toxic and side effect of the cisplatin and still retains the antitumor property. Clinical applications show that biochemical and physical characteristics of carboplatin are similar to those of cisplatin, but its nephrotoxicity, ototoxicity, and neurotoxicity, especially gastrointestinal reactions, are significantly lower than those of cisplatin, and thus carboplatin has become a broad-spectrum antitumor drug that has received extensive attention for more than a decade. Like cisplatin, carboplatin is a cell cycle non-specific drug, it mainly acts on the $N^7$ and $O^6$ atoms of guanine in DNA, thereby causing inter-strand and intra-strand cross-linking of DNA, destroying the replication of DNA molecules, and resulting in tumor cell apoptosis.

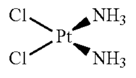

Cisplatin

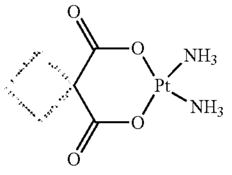

Carboplatin

In addition to cisplatin and carboplatin, a variety of platinum-based anticancer drugs have entered the research and clinical stage. In addition to the issue of toxic reactions, the stability of these drugs, especially in aqueous solutions, has become a fatal disadvantage for their clinical applications. Therefore, improvement and modification of drugs with existing structures are being implemented all the time.

On the other hand, the resistance issue of chemotherapy drugs is also a bottleneck affecting tumor treatment, where after tumor cells are in contact with a drug for many times, the sensitivity to the drug decreases or even disappears, resulting in a decrease or ineffectiveness of the drug's efficacy. Once drug resistance occurs, the chemotherapeutic effect of drug will be significantly reduced, and continued administration of drug will lead to treatment failure. At the same time, when tumor cells become resistant to one anticancer drug, they may also develop cross-resistance to other anticancer drugs with different structures and mechanisms of action, where this Multiple Drug Resistance (MDR) or Cross Resistance is the most important reason for the failure of tumor chemotherapy, and there is still no good strategy in clinical practice. With the development of translational medicine, it has been revealed that tumor-driving gene mutations facilitate the occurrence and development of tumors through different signaling pathways and mechanisms, paving a way for tumor-targeted therapy. However, inevitably, drug resistance also occurs in the targeted therapy after 8-14 months of treatment, and solving the issue of drug resistance is still a challenge to successful tumor treatment.

The continuous research and development and approval of new drugs are of course the pursuit of pharmaceutical field, and the upgrading of classic anti-cancer, anti-viral, and anti-bacterial drugs is also an important idea and direction to improve therapeutic efficacy and expand indications.

SUMMARY

The present disclosure provides a carboplatin complex, where 1,1-cyclobutanedicarboxylic acid molecules are introduced into a carboplatin molecule through bonding of hydrogen bonds, the water solubility, stability, bioavailability and other functions of carboplatin are improved, thereby obtaining a platinum-based pharmaceutical preparation with reduced toxicity.

The present disclosure further provides a pharmaceutical preparation containing the above carboplatin complex as an active component, which not only has good stability, but also has clear efficacy.

The present disclosure further provides preparation methods of the above carboplatin complex and pharmaceutical preparation. By controlling and optimizing a treatment process, a stable complex formed by carboplatin and 1,1-cyclobutanedicarboxylic acid through non-covalent bonds is achieved, which has very high purity as a target product.

The present disclosure further provides use of the above carboplatin complex in preparation of an antitumor drug, an antibacterial drug, an antifungal drug, or an antiviral drug, thereby improving drug targeting and reducing toxic and side effects of drug.

The present disclosure further provides a quality control method for the above carboplatin complex as a bulk drug, which can ensure the quality controllability and safety of the carboplatin complex used in the production of pharmaceutical preparations.

A first aspect of the present disclosure provides a carboplatin complex, which is a complex formed by combining carboplatin and 1,1-cyclobutanedicarboxylic acid through two hydrogen bonds, where each of the two hydrogen bonds is formed between a carbonyl oxygen of a carboplatin molecule and a carboxyl hydrogen of a 1,1-cyclobutanedicarboxylic acid molecule.

Specifically, the above carboplatin complex may be a complex formed from one molecule of carboplatin and one molecule of 1,1-cyclobutanedicarboxylic acid through intermolecular hydrogen bonds. For the structure of the carboplatin complex provided by the present disclosure, it may be shown as follows:

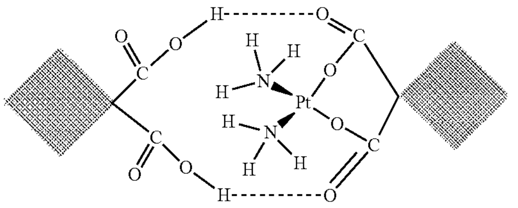

This structure illustrates a main product formed by the combination of the carboplatin and the 1,1-cyclobutanedicarboxylic acid, its molecular formula may be represented as $C_6H_{12}N_2O_4Pt{\cdot}C_6H_6O_4$, and its molecular weight may be 515.0917.

As described above, carboplatin is a product obtained by a substitution reaction between the cisplatin and the 1,1-cyclobutanedicarboxylic acid, where two chlorine atoms in a cisplatin molecule are substituted with 1,1-cyclobutanedicarboxylic acid. Among a mixture formed in carboplatin synthesis, in addition to free monomolecular cisplatin, carboplatin and 1,1-cyclobutanedicarboxylic acid, there will also be some components with relatively large molecular weight. Further investigation of the composition of these impurities leads the inventors to focus on specific products formed by further self-assembling the carboplatin with the 1,1-cyclobutanedicarboxylic acid through hydrogen bonding. Further analysis and detection show that the "impurity" is actually a complex formed by the carboplatin and free 1,1-cyclobutanedicarboxylic acid in a molar ratio of 1:1, through hydrogen bonding and geometric space. Studies also find that the complex is extremely disordered and unstable as a "chemical drug", and is very sensitive to acid and alkali, temperature, optical spectrum, chromatography, electromagnetic field, etc., and it is easily decomposed into the carboplatin and the free 1,1-cyclobutanedicarboxylic acid. However, under mild conditions (below 80° C., PH 2-7.5, in the dark, etc.), the complex is fully stable. Furthermore, the inventor's research also finds that the structure of the complex is similar to that of DNA base pairs, where carboplatin and 1,1-cyclobutanedicarboxylic acid are also assembled together through two hydrogen bonds and geometric spatial structure, and many features of the complex are also similar to those of DNA base pairs. In a suitable environment, for example, when an enzyme (helicase) is active, hydrogen bonds may be broken and the activity of carboplatin is released.

In order to further study the bonding of carboplatin with 1,1-cyclobutanedicarboxylic acid, the present disclosure adopts a nuclear magnetic resonance titration method ($^1$HNMR) using deuterated dimethylsulfoxide (DMSO) as a solvent (it is generally recognized that it is equivalent to the influence of water environment on an object to be tested.) to study the chemical shifts of hydrogen of the carboplatin and the 1,1-cyclobutanedicarboxylic acid in a mixed condition. Results show that, when the amount of 1,1-cyclobutanedicarboxylic acid is constant, with the increase of the amount of carboplatin, only the chemical shift change in carboxyl hydrogen occurs in the titration results of a mixture of the two components, while that in amino hydrogen does not occur. It can be inferred that the self-assembly between carboplatin and 1,1-cyclobutanedicarboxylic acid is achieved by the carboxyl hydrogen.

The toxicity of platinum drugs comes from coordination bonds of platinum, the active coordination bond of platinum atom may bond with G-N7 in DNA to form a stronger adduct. The reduction of side effects of platinum drugs is to slow down the rate and efficiency of adduct formation. When carboplatin and 1,1-cyclobutanedicarboxylic acid form a complex, that is, a complex substrate having a structure similar to DNA base pairs A-T/G-C, the carboplatin molecule is a host, and the 1,1-cyclobutanedicarboxylic acid molecule is a guest for providing hydrogen bonds, then the drug activity of the host is effectively blocked by the gust molecule to form a complex with no or very low DNA toxicity, thereby having no toxicity to normal non-replicating cells.

In a further embodiment of the present disclosure, the carboplatin complex is derived from a self-assembled product of the carboplatin and the 1,1-cyclobutanedicarboxylic acid, and a mass content of the carboplatin complex is 95% or more.

A self-assembled product in high purity can be obtained through an appropriate process control, thereby providing ideas and directions for achieving platinum drugs with better aspects such as water-soluble stability, anti-tumor spectrum, toxic and side effects, and mechanism of action on the basis of carboplatin. In order to distinguish it from carboplatin, this kind of carboplatin complex is abbreviated as "carboplatin 4.0" in the present disclosure. That is to say, the carboplatin 4.0 provided by the present disclosure takes the self-assembled product of carboplatin and 1,1-cyclobutanedicarboxylic acid as a main component, where the self-assembly rate is 95% or more. By controlling the appropriate preparation process, the self-assembly rate can reach 96% or more, or 98% or more, or even up to 99% or more.

The carboplatin complex structure provided by the present disclosure includes carboplatin and 1,1-cyclobutanedicarboxylic acid combined by hydrogen bonding. As for the carboplatin complex, a phase transition peak starts to form (i.e., melting and decomposing begin, generally forming a sharp phase transition peak) at about 197.8±2° C. in results measured by differential scanning calorimetry (DSC), and/or, there is no diffraction peak at 2θ of about 11.55±0.2° in results measured by X-ray powder diffraction analysis (XRPD).

Specifically, in the above XRPD measurement results, the diffraction peak at 2θ of about 11.55±0.2° is the characteristic peak of carboplatin. It can be understood that, due to the influence of samples, detection conditions, etc., the above detection results may have certain deviations, and all diffraction peaks appearing at around 11.55° (such as 11.55±0.2°) may be usually characterized as the characteristic peaks of carboplatin. According to the research results of the present disclosure, in the XRPD measurement results of the carboplatin complex, there are generally diffraction peaks at 7.55°, 10.51°, 14.63°, 15.10°, 15.66°, 16.78°, 18.55°, 20.83°, 22.86°, 23.67°, 24.02°, etc., these diffraction peaks may be used as the characteristic peaks of the above carboplatin complex, and their deviations may all be in the range of ±0.2° (e.g., the above diffraction peak at 2θ of 7.55° may be the diffraction peak at 7.55±0.2°).

The present disclosure further provides a pharmaceutical preparation, containing the carboplatin complex as an active component.

According to the classification in the pharmaceutical field, the pharmaceutical preparation provided by the present disclosure is mainly used as an antitumor preparation, an antibacterial preparation, an antifungal preparation, or an antiviral preparation.

Specifically, the pharmaceutical preparation is in a form of a liquid injection, a lyophilized powder injection, an oral solid preparation, a gel preparation, or a spray preparation.

In the pharmaceutical preparation provided by the present disclosure, the carboplatin complex (i.e., carboplatin 4.0) is the active component, where 1,1-cyclobutanedicarboxylic acid actually plays a role of pharmaceutical excipients. The research of the present disclosure shows that 1,1-cyclobutanedicarboxylic acid is used as a pharmaceutical excipient for carboplatin 4.0 due to its molecular particularity. Firstly, the 1,1-cyclobutanedicarboxylic acid itself is an important raw material for production of carboplatin; secondly, the 1,1-cyclobutanedicarboxylic acid and carboplatin can form the most suitable stable complex substrate through hydrogen bonding; besides, due to the excipient effect of the 1,1-cyclobutanedicarboxylic acid, the water solubility, stability, bioavailability, helicase targeting and other functions of the carboplatin are changed and improved. Furthermore, the 1,1-cyclobutanedicarboxylic acid is also produced when the carboplatin binds to DNA, demonstrating that the 1,1-cyclobutanedicarboxylic acid has a clear structure, controllable quality and chemical stability, and accordingly, trace amounts of 1,1-cyclobutanedicarboxylic acid is also safe for organisms.

Based on studies on the property and efficacy of the above carboplatin complex, the present disclosure further provides use of the carboplatin complex in manufacture of a drug, such as an antitumor drug, an antibacterial drug, an antifungal drug, or an antiviral drug.

Based on in-depth studies on the structure and characteristics of the above carboplatin complex, the applicant believes that the carboplatin complex with the features described in the present disclosure is more precisely a new preparation of carboplatin, which can be understood as a pharmaceutical preparation similar to liposome entrapment. In the case that the antitumor efficacy of carboplatin is already beyond doubt, the following mechanism of action may also be verified by experimental results: the complex of a host/guest structure obtained by the carboplatin and 1,1-cyclobutanedicarboxylic acid through hydrogen bonding is prepared into a new pharmaceutical preparation, which may be broken under conditions with helicase activity and release a single carboplatin molecule and a single 1,1-cyclobutanedicarboxylic acid molecule, in other words, the hydrogen bond of the complex is a target for a helicase and the complex (carboplatin 4.0) may be considered as the complexing substrate for the helicase.

Therefore, combined with the above mechanism researches, it may be believed that the drug provided by the present disclosure refers to a targeting drug system in which the hydrogen bonds in an active component molecule serve as a target for a helicase. The targeting drug may include an antitumor drug, an antiviral drug, an antibacterial drug, an antifungal drug, and so on.

The present disclosure further provides a method of preparing the above carboplatin complex, especially by optimizing and purposely controlling the operating conditions, the self-assembling of carboplatin and 1,1-cyclobutanedicarboxylic acid is achieved, thereby preparing the target product with a purity or content as high as possible that meets the above characteristics.

The preparation method includes following operation processes (self-assembly conditions):

mixing the carboplatin and the 1,1-cyclobutanedicarboxylic acid in a molar ratio of 1:(1.5-3), at 65° C.±10° C. for not less than 0.5 hours, so as to prepare a supersaturated aqueous solution; and collecting crystals of the carboplatin complex (i.e., self-assembled product).

The above supersaturated aqueous solution refers to the supersaturated aqueous solution of the complex formed by carboplatin and 1,1-cyclobutanedicarboxylic acid. Typically, a certain concentration of carboplatin aqueous solution may be prepared first, and then 1,1-cyclobutanedicarboxylic acid may be added to the carboplatin aqueous solution, where, under the above self-assembly conditions, the concentration of each raw material is as high as possible, and at the same time, a state without crystal precipitation is maintained, and it may be considered that the solution prepared is supersaturated aqueous solution.

It is found by the applicant's research that the aqueous solution of a mixture of carboplatin and 1,1-cyclobutanedicarboxylic acid may also naturally generate an unstable complex, and different amounts of complex may also be generated under different conditions, even a physical powder mixture of carboplatin and 1,1-cyclobutanedicarboxylic acid may generate the molecular information of a small amount of complex. In this case, the preparation method provided by the present disclosure optimizes the conditions of the solution system formed by carboplatin and 1,1-cyclobutanedicarboxylic acid, so that a mixed solution system is obtained in which there is a significant excess amount of the 1,1-cyclobutanedicarboxylic acid and each of the two reaction raw materials has a concentration as high as possible so as to enable the resulting complex to be in a supersaturated state. Furthermore, maintaining an appropriate controlled temperature for a certain period of time (in general, more than 1 hour is sufficient, for example, it may be maintained for 3 or 4 hours.) is beneficial for the formation of an ordered and stable complex between the carboplatin molecule and the 1,1-cyclobutanedicarboxylic acid molecule through non-covalent bonds, that is to obtain a high yield of the carboplatin complex. At the same time, free monomolecular carboplatin and 1,1-cyclobutanedicarboxylic acid are considered as impurities and reduced to extremely low trace amounts. The self-assembled product is in a crystalline state. The reaction system is cooled to be room temperature or lower to precipitate crystals, which is subjected to separation treatment to obtain a product with relatively high purity appearing as nearly colorless crystals. More than one recrystallization may be performed after separation so as to improve the purity of the product. It can be understood that the use of raw materials in high purity is also an effective means to improve the purity and yield of the product.

In the above assembly process, through optimizing the mixing ratio (molar ratio) of carboplatin and 1,1-cyclobutanedicarboxylic acid in the aqueous solution, and factors such as temperature and assembly time as well, so that the two components assemble into a stable complex in the aqueous solution, and after crystallization separation and purification, the carboplatin complex with high self-assembly rate is obtained. In an embodiment of the present disclosure, as required, the prepared supersaturated solution may be filtered to collect a filtrate, which is placed in the dark at room temperature (usually, 20° C.±5° C.), usually for not less than 7 days, so as to facilitate the precipitation of crystals of the complex, so that the purity and yield of the carboplatin complex are further improved.

Unless otherwise specified, the yield of carboplatin complex, the content of carboplatin complex in the self-assembled product system, and the self-assembly rate mentioned in the present disclosure are all understood to have the same meaning.

On the basis of obtaining the above carboplatin complex, a pharmaceutical preparation with the carboplatin complex as an active component is further prepared, the method for preparing the pharmaceutical preparation comprising:

- preparing crystals of the carboplatin complex according to the previously described method, grinding and drying, so as to obtain a powder of the carboplatin complex; and
- preparing the powder of the carboplatin complex into a preparation.

Specifically, the carboplatin complex may be first prepared into a mother liquid, and then into a liquid injection, or a lyophilized powder injection and the like as follows:

- dissolving the powder of the carboplatin complex in sterilized water, stirring and dissolving at 45° C.±5° C., and standing at room temperature for 1 hour or more, so as to obtain a mother liquid;
- filtering and sterilizing the mother liquid at room temperature, and then packaging into a liquid injection; or
- preparing the mother liquid into a lyophilized powder injection, an oral solid preparation, a gel preparation, or a spray preparation, etc.

In the present disclosure, 1,1-cyclobutanedicarboxylic acid is utilized as an excipient of the new carboplatin preparation, thereby making the carboplatin complex powder preparation become a very stable liquid injection, which is similar to liposome entrapment technique. A specific example of preparing a liquid injection may include: dissolving 500 g carboplatin complex powder in sterile water, and rationing with sterile water to 500 L; stirring and dissolving evenly at 45° C.±5° C., placing at room temperature for not less than 1 hour so as to obtain a mother liquid for preparation, and performing a content detection; when it is satisfied with the standard via the content detection, filtering the prepared mother liquid and sterilizing at room temperature, and packaging to obtain a liquid injection in 5 mg/5 ml, and storing at a low temperature (4° C.-10° C.) in the dark.

In the embodiments of the present disclosure, after the expected carboplatin complex (which can be referred to as carboplatin 4.0) is prepared, the complex may be prepared into corresponding pharmaceutical dosage forms based on common means in the pharmaceutical field. In addition to injection preparation, it may also be in the form of oral preparation, or topical administration preparation such as gel preparation and spray preparation.

Another aspect of the present disclosure provides a quality control method for the above carboplatin complex.

Research of the inventor finds that, although chromatography-mass spectrometry (LC-MS) analysis is a preferred method for the determination of the content of most synthetic products, in view of the two molecules in the carboplatin complex bound only by hydrogen bonds, chromatographic separation would disrupt hydrogen bonds, which may mislead test results due to the release of the carboplatin and the 1,1-cyclobutanedicarboxylic acid. The accurate molecular weight of the carboplatin 4.0 may be obtained in negative ion mode by direct mass spectrometry analysis after sampling by flow injection, but a physical mixture of the carboplatin and the 1,1-cyclobutanedicarboxylic acid (hereafter referred to as the two-component physical mixture) may also produce the same ions in this mode; therefore, even if the molecular weight can be accurately measured, it cannot be used as the basis for measuring the content of the carboplatin 4.0.

Capillary electrophoresis analysis shows that carboplatin 4.0, carboplatin, 1,1-cyclobutanedicarboxylic acid and other samples are identified by three modes, which are aqueous capillary zone electrophoresis (CZE), non-aqueous capillary zone electrophoresis (NACZE) and micellar electrokinetic capillary chromatography (MEKC). Under the above various optimized identification conditions, none of the above samples show separation phenomenon, and the peak appearance times of carboplatin 4.0 and carboplatin are consistent. Combined with the analysis results of $^1$HNMR and LC-MS, it is further demonstrated that carboplatin 4.0 dissociates into carboplatin and 1,1-cyclobutanedicarboxylic acid under the action of electric field energy, due to the existence of intramolecular hydrogen bonds that are relatively weaker than covalent bonds.

Furthermore, there is no obvious difference on infrared spectra between carboplatin 4.0 (or its lyophilized powder formed after being dissolved in water and then lyophilized) and the above two-component physical mixture, and the infrared spectrum analysis is also not suitable for quantitative and qualitative analysis of carboplatin 4.0.

On the other hand, when the X-ray powder diffraction analysis (XRPD) is used, there are obvious differences on characteristics of the diffraction peaks between the above carboplatin complex with hydrogen bonding and carboplatin in the XRPD measurement chart. In other words, the characteristic peak of carboplatin appears around the diffraction angle of 11.55±0.2°, while carboplatin 4.0 has almost no diffraction peak at this position and its main characteristic peaks appear at positions where the 2θ angle is each 7.55°, 10.51°, 14.63°, 15.10°, 15.66°, 16.78°, 18.55°, 20.83°, 22.86°, 23.67°, 24.02°, etc. (their deviation may all be in the range of ±0.2°). Of course, further detection of absorption peaks of carboplatin and 1,1-cyclobutanedicarboxylic acid with chromatography and mass spectrometry is also a necessary step for product quality control.

According to the research results of the present disclosure, although the direct content determination method of carboplatin 4.0 cannot be established by some existing analytical methods, the indirect content determination of carboplatin 4.0 may be achieved by measuring the contents of carboplatin and 1,1-cyclobutanedicarboxylic acid. Therefore, the following quality control methods may be established for the carboplatin 4.0: (1) based on the differences among the characteristic diffraction peaks of carboplatin 4.0, carboplatin and 1,1-cyclobutanedicarboxylic acid, XRPD method is used so as to achieve the control of limit test of free carboplatin in carboplatin 4.0; (2) since carboplatin 4.0 is formed by one molecule of carboplatin and one molecule of 1,1-cyclobutanedicarboxylic acid by hydrogen bonding, and is easily dissociated under polar solvent conditions to generate the carboplatin and the 1,1-cyclobutanedicarboxylic acid, the molar ratio of carboplatin and 1,1-cyclobutanedicarboxylic acid and the contents of both may be determined using high performance liquid chromatography (HPLC) and included in the quality control standard for carboplatin 4.0.

Accordingly, the present disclosure provides a quality control method for a carboplatin complex, comprising: detecting a test sample by X-ray powder diffraction analysis, and determining that the test sample has no diffraction peak at 2θ of about 11.55±0.2°; the test sample at this position may include the above carboplatin complex, or the above pharmaceutical preparation containing the carboplatin complex as an active component.

It can be understood that the quality control method of the present disclosure is aimed at the carboplatin complex (carboplatin 4.0), and this method may also be used for quality control of the purity of carboplatin 4.0 bulk drug. Generally, the content of free carboplatin in the bulk drug is required to be not more than 2%, and in more precise cases, it may be not more than 1%.

According to the XRPD measurement results of carboplatin 4.0, the carboplatin 4.0 has no characteristic peak at 2θ of about 11.55±0.2°, and has diffraction peaks at positions where 2θ is about 7.55°, 10.51°, 14.63°, 15.10°, 15.66°, 16.78°, 18.55°, 20.83°, 22.86°, 23.67°, 24.02°, etc. (their deviations may all be in the range of ±0.2°), where, the diffraction peak at 2θ of about 15.10±0.2° may be regarded as a semi-quantitative characteristic peak of carboplatin 4.0. Based on this, a relative integral area of the characteristic peak at 2θ of about 15.10±0.2° and the characteristic peak of carboplatin (a diffraction peak at 2θ of about) 11.55±0.2° may be used as quantitative standards, so as to achieve the limit test of free carboplatin.

Specifically, in the XRPD measurement results of the test sample which is carboplatin 4.0, if a diffraction peak at 2θ of about 11.55±0.2° is detected, the integral area of the diffraction peak at 2θ of about 11.55±0.2° will be recorded as A1 and the integral area of the diffraction peak at 2θ of about 15.10±0.2° will be recorded as A2, so the content of free carboplatin in carboplatin 4.0 may be determined by a value of A1/A2. For example, in an embodiment of the present disclosure, in order to achieve effective control of the content of free carboplatin in carboplatin 4.0 bulk drug (carboplatin 4.0 test sample), based on the XRPD measurement results of the carboplatin 4.0 test sample, the value of A1/A2 should not be greater than a corresponding integral area ratio of a mixed sample (or mixed reference), which is prepared from carboplatin 4.0 and carboplatin accounting for x % of the carboplatin 4.0 by mass, so as to ensure that the content of the free carboplatin will not exceed x %. In a specific implementation, x % may be, for example, 1%, 0.5%, 0.1%, and so on. The carboplatin 4.0 used to prepare the above mixed sample has basically no diffraction peak detected at 2θ of about 11.55±0.2°, and so it may generally be considered to be pure carboplatin 4.0.

In a specific embodiment of the present disclosure, the mixed sample of carboplatin 4.0 and carboplatin is prepared, where the carboplatin accounts for 1% by mass of carboplatin 4.0 (i.e., the x %=1%); the mixed reference and the carboplatin 4.0 bulk drug are measured by XRPD, where the value of A1/A2 measured for the above mixed reference is about 0.67, so the value of A1/A2 measured for the carboplatin 4.0 bulk drug should be not greater than 0.67, thereby ensuring that the content of the free carboplatin in the bulk drug does not exceed 1%. In another embodiment, the above x % may be specifically 0.5%, where the value of A1/A2 measured for the mixed reference is about 0.55, so the value of A1/A2 measured for the carboplatin 4.0 bulk drug should be not greater than 0.55, thereby ensuring that the content of the free carboplatin in the bulk drug does not exceed 0.5%. In yet another embodiment, the above x % may be specifically 0.1%, where the value of A1/A2 measured for the mixed reference is about 0.5, so the value of A1/A2 measured for the carboplatin 4.0 bulk drug should be not greater than 0.5, thereby ensuring that the content of the free carboplatin in the bulk drug does not exceed 0.1%.

Alternatively, in another embodiment, another limit test method may be provided: the intensity (or integral area) of the diffraction peak of carboplatin 4.0 bulk drug at 2θ of 11.55±0.2° should be not greater than the intensity (or integral area) of the diffraction peak of the mixed sample at the same 2θ, where the mixed sample is prepared from carboplatin 4.0 and carboplatin accounting for x % by mass of the carboplatin 4.0; where, as described above, x % may be, for example, 1%, 0.5%, 0.1%, and so on.

The quality control method provided by the present disclosure further includes: detecting the carboplatin 4.0 test sample by HPLC method, and determining that the contents of carboplatin and 1,1-cyclobutanedicarboxylic acid in the test sample are each 97%-103%, and a molar ratio of carboplatin and 1,1-cyclobutanedicarboxylic acid is 0.95-1.05. In other words, according to the quality control method of the present disclosure, in addition to determining the characteristics of diffraction peaks under XRPD, moreover, it is required to detect by HPLC method carboplatin and 1,1-cyclobutanedicarboxylic acid that are released after hydrogen bond breakage. The results of them should be 97%-103% of their own theoretically existing amounts in a combined state, respectively, and carboplatin and 1,1-cyclobutanedicarboxylic acid generally exist in a molar ratio of 1:1, and the control standard should be in the range of ±0.05 (i.e., the molar ratio of the two is about 0.95-1.05).

Researches of the inventor find that by HPLC method analysis, the concentration of carboplatin shows a good linear relation with and the integral value of the chromatographic peak area of the carboplatin in a range of 0.025-0.999 mg/mL, where, an equation of linear regression is Y=40169+8.62E6X and a correlation coefficient r=0.999; the concentration of the 1,1-cyclobutanedicarboxylic acid shows a good linear relation with the integral value of the chromatographic peak area of the 1,1-cyclobutanedicarboxylic acid in a range of 0.101-3.99 mmol/L, where, an equation of linear regression is Y=7407+962202X and a correlation coefficient r=0.999. From this, in an embodiment of the present disclosure, HPLC detection may be performed on the carboplatin 4.0 test sample, and the mixed reference of carboplatin and 1,1-cyclobutanedicarboxylic acid; based on the measurement results, the contents and the molar concentration ratio (molar ratio) of carboplatin and 1,1-cyclobutanedicarboxylic acid in the carboplatin 4.0 test sample are determined by the peak area according to an external standard method.

In an embodiment of the present disclosure, when determining the content/molar ratio, the carboplatin 4.0 test sample is prepared with a mobile phase for test into a test sample solution with a concentration of the carboplatin 4.0 of about 1.0 mg/mL (calculated based on the theoretical amount), and a carboplatin reference substance and a 1,1-cyclobutanedicarboxylic acid reference substance are used to prepare a mixed reference test solution, where the concentrations of the two are about 0.7 mg/mL and 0.3 mg/mL, respectively, for HPLC detection.

The present disclosure not only provides a carboplatin complex (carboplatin 4.0) formed by specific hydrogen bonding, but also provides a pharmaceutical preparation made with the carboplatin complex, and in particular provides a targeting drug that serves as a target of a helicase, which is expected to become an upgraded version of a carboplatin drug. The present disclosure further provides a feasible quality control method for the prepared carboplatin 4.0 as bulk drug, and the activity and pharmacokinetics of the carboplatin 4.0 are investigated using the carboplatin as a control.

According to the research results of the present disclosure, since carboplatin 4.0 is dissociated to release carboplatin, therefore, it may be completely reasonably expected that clinical indications include all indications of the carboplatin bulk drug. Currently, the carboplatin is clinically mainly used for treating small cell lung cancer, ovarian cancer, testicular cancer, germ cell tumor, thyroid cancer and nasopharyngeal cancer, and also can be used for treating a malignant tumor, such as cervical cancer, non-small cell lung cancer, esophagus cancer, seminoma, bladder cancer, mesothelioma, pediatric brain tumor and other head and neck cancers. A patient who cannot tolerate cisplatin due to renal impairment, refractory vomiting, hearing loss, or neurotoxicity is more likely to select carboplatin 4.0 as an upgraded drug. The indications are more likely to be expanded to brain tumors or brain metastases, bone tumors or bone metastases, prostate cancer, pancreatic cancer, biliary duct cancer, etc., in other words, there is a broader spectrum of indications. At the same time, the carboplatin 4.0 is also suitable for the treatment on other platinum-resistant patients and combination with targeted drug therapy; it has no clinical cross resistance with other chemotherapeutic drugs, and can be used alone or in combination with other chemotherapeutic drugs, and can be used in combination with surgery and radiotherapy to improve a therapeutic effect.

In a specific implementation, carboplatin 4.0 is used to study the chemosensitivity of eight kinds of oxaliplatin- or irinotecan-resistant colon cancer cells and their primary cells. Results show that carboplatin 4.0 has no cross resistance reaction with oxaliplatin and irinotecan, and thus carboplatin 4.0 may be considered as another chemotherapy option for patients with clinically resistant colon cancer.

On the other hand, since the platinum atom of carboplatin is blocked by another molecule, 1,1-cyclobutanedicarboxylic acid, this will hinder the binding of platinum atom to DNA, which significantly reduces the toxic activity of carboplatin 4.0 to DNA.

According to the inventor's research, carboplatin 4.0 and carboplatin are each subjected to a binding assay with a linear DNA, and results show that, in a certain period of time, the carboplatin quickly forms a cross-linked adduct with DNA, and the linear DNA deforms, shrinks, and condenses; but there is no cross-linking reaction between the carboplatin 4.0 and the linear DNA and the shape of linear DNA basically does not change. Furthermore, the carboplatin 4.0 and the carboplatin are each mixed with supercoiled plasmid DNA, and after a period of time, the electrophoresis results show that the carboplatin crosslinks with the supercoiled plasmid DNA to form a adduct, while the carboplatin 4.0 does not crosslink with supercoiled plasmid DNA and its movement rate is consistent with that of the supercoiled plasmid DNA of a blank control group without adding any platinum drug. The above research results demonstrate that, in the structure of carboplatin 4.0, the platinum atom of carboplatin is blocked and covered by another molecule of 1,1-cyclobutanedicarboxylic acid, and it is such blocking and covering that hinders the binding of the platinum atom to DNA, which significantly reduces the toxic activity of carboplatin 4.0 to DNA.

Results of the pharmacokinetic study show that, compared with carboplatin, the half life (t½) of the drug clearance of carboplatin 4.0 is significantly faster. Since carboplatin 4.0 exhibits better solubility and non-polarity than carboplatin, it has short clearance half life in organs of an organism, higher clearance rate, and significantly reduced toxic and side effects, especially the incidence of nephrotoxicity. The absolute bioavailability of carboplatin 4.0 and carboplatin is basically the same, however, compared with carboplatin, the carboplatin 4.0 has the advantages of low binding to plasma proteins, fast transmembrane transport, no damage to non-replicating cells and so on, and thus also exhibits higher bioavailability. Furthermore, in terms of apparent volume of distribution (Vd), compared with carboplatin, carboplatin 4.0 is more widely distributed, especially in tissues and organs with barriers, such as brain tissue, bone marrow, and prostate, indicating that the carboplatin 4.0 has wider clinical indications.

The research of the present disclosure also indicates that, in addition to being superior to carboplatin in antitumor performance, carboplatin 4.0 is expected to become an upgraded antitumor drug of carboplatin. Carboplatin 4.0 also has excellent performance in antiviral, antifungal and antibacterial aspects, therefore, it indicates a wider range of indications, including obvious inhibition effects on hand-foot-mouth virus (EV71 virus), influenza virus (H3N2), HSV-1 virus, EB virus, HPV virus, bacteriophages, indicator bacteria, Candida albicans, etc.

Furthermore, the inventors have evaluated the application of carboplatin 4.0 and carboplatin in an antiviral aspect through the data of cytotoxicity experiments, and results show that the cytotoxicity of carboplatin hinders its application in the antiviral aspect. The carboplatin 4.0 passed the impact evaluation of the drug effectiveness, drug toxicity, drug resistance, and effects of drugs on apoptosis and proliferation of cells in the cytotoxicity test.

Another aspect of the present disclosure further provides a method of treating a malignant tumor disease, comprising: administering a drug comprising the above carboplatin complex as an active component to a patient, or administering the above pharmaceutical preparation.

Another aspect of the present disclosure further provides a method of treating bacterial or fungal infection, comprising: administering a drug comprising the above carboplatin complex as an active component to a patient, or administering the above pharmaceutical preparation.

Another aspect of the present disclosure further provides a method of treating viral infection, comprising: administering a drug comprising the above carboplatin complex as an active component to a patient, or administering the above pharmaceutical preparation.

The carboplatin complex provided by the present disclosure is formed by combining carboplatin and 1,1-cyclobutanedicarboxylic acid through two hydrogen bonds, where intermolecular hydrogen bonds improve the water solubility, stability, bioavailability and other functions of carboplatin, and compared with carboplatin, the carboplatin complex has greatly reduced toxic and side effects and extremely low drug resistance/cross resistance, and also has a wider range of indications in antitumor, antiviral, antifungal, and antibacterial aspects.

BRIEF DESCRIPTION OF THE DRAWINGS

FIG. 3 is a DSC measurement diagram of 1,1-cyclobutanedicarboxylic acid, carboplatin, mixed powder c, lyophilized powder b, carboplatin 4.0 bulk drug, and lyophilized powder a;

FIG. 6 is an XRPD diagram of mixed powder c, lyophilized powder b, carboplatin 4.0 bulk drug, and lyophilized powder a;

FIG. 7 is the chromatogram of total ion currents of carboplatin in a positive ion mode, (retention time RT=0.83 min);

DETAILED DESCRIPTION OF THE EMBODIMENTS

Figure 1:
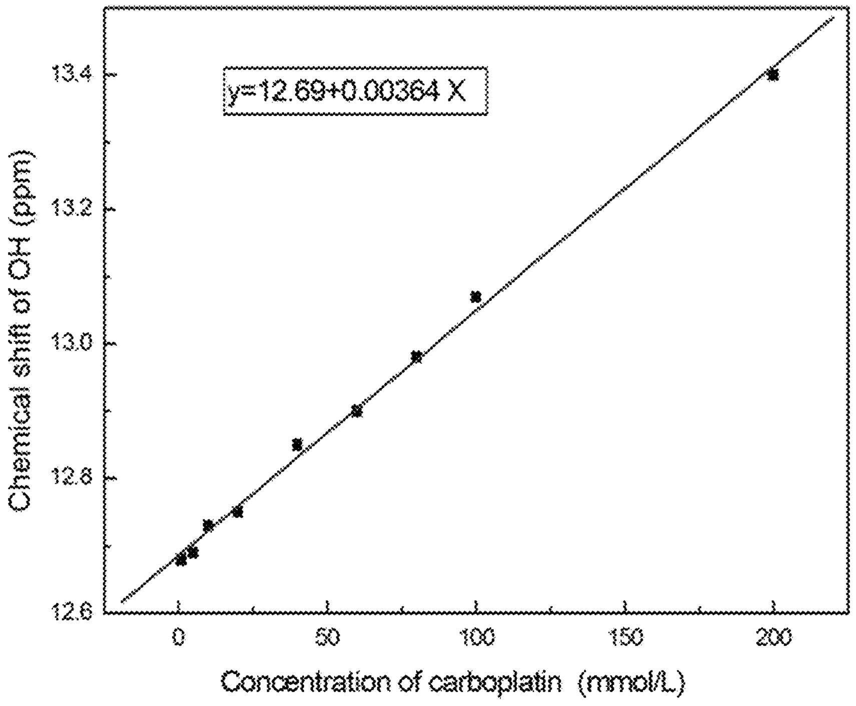
FIG. 1 is a diagram showing the change of the chemical shift of carboxyl hydrogen (OH) with the increase of concentration of carboplatin.

In combination with the examples, the contents of the present disclosure will be described in more details below. It should be understood that the implementation of the present disclosure is not limited to the following examples, and any modifications and/or changes in the form of the present disclosure will fall within the protection scope of the present disclosure.

In the following examples, unless otherwise specified, all the processes involved (such as temperature control, temperature rise, measuring, collecting, formulation of detection liquid for testing, detection process, etc.) can adopt conventional processing means in the art, for example, the use of conventional instruments, methods, etc., for corresponding treatment.

In the following examples, the involved instruments and related test conditions are as follows:

1) Nuclear Magnetic Resonance Titration Method ($^1$HNMR)

JEOL ECA-400 type superconducting Fourier Transform Nuclear Magnetic Resonance Spectrometer, equipped with a selective pulse Laminal waveform generator and 5 mm z-axis gradient pulse multinuclear probes. $^1$H operating frequency is 400 MHz, DMSO-d6 is used as a solvent, TMS is used as an internal standard, the experimental temperature is room temperature, and Φ5 mm multinuclear probes are used. The spectral width of $^1$HNMR is 9.18 kHz, the data point is 32768, the 90° pulse width is 11 μs, and the relaxation delay is 1.2 s.

2) Differential Scanning Calorimetry (DSC)

The analytical instrument is American TA Q2000, where Al plate is a reference plate, and sample plate is an aluminum plate; and heating rate is 10° C./min, and heating range is 40° C.-240° C.

3) X-Ray Powder Diffraction (XRPD)

X-ray powder diffractometer (Bruker D8-advance, equipped with a reflection-transmission rotating sample stage);

- Transmission: CuKα radiation, a focusing monochromator, gobel-mirror focusing optical path, tube voltage: 40 kV, and tube current: 40 mA;
- Scanning mode: θ/2θ scanning; DS divergence slit: 1.2 mm, Soller slit: 2.5 mm;
- 2θ scanning range: 6-50°; scanning speed: 0.4 s/step; step size: 0.015°/step.

4) Liquid Chromatography-Mass Spectrometry (LC-MS)

- Instrument: Shimadzu LCMS-8040
- Capillary voltage: 3 KV (or −2.6 KV)
- Extractor voltage: 4 V (or −4 V);
- Sample cone voltage: 15 V (or −20 V);
- Source temperature: 300° C.;
- Scanning range: 80-1000 amu;
- Chromatographic column: XDB-C18, 4.6×50 mm, 1.8 μm;
- Mobile phase A: 0.1% formic acid aqueous solution;
- Mobile phase B: methanol;
- Gradient: 0 min, 99% A and 1% B; 1 min, 99% A and 1% B; 3.5 min, 40% A and 60% B; 5.5 min, 40% A and 60% B;
- Flow rate: 0.5 mL/min;
- Injection volume: 2 μL.

In the following examples, carboplatin is purchased from Qilu Pharmaceutical Co., Ltd., and 1,1-cyclobutanedicarboxylic acid is a product from MERCK Company in Germany

Example 1. A Self-Assembly Process of Carboplatin 4.0 and Preparation of Its Liquid Injection

1. A Self-Assembly Process of Carboplatin 4.0

1) carboplatin and 1,1-cyclobutanedicarboxylic acid with their respective purity of not less than 99% were mixed in a molar ratio of 1:2, so as to prepare a supersaturated aqueous solution (the concentration of each component was as high as possible, and no crystallization was maintained); where such mixing and preparation operation was implemented at 65° C.±5° C. for about 4 hours to complete the self-assembly reaction;

2) the reaction system was filtered, and the filtrate was kept at room temperature (20±5° C.) for 10 days in the dark, and the formation of crystals could be observed;

3) the solution was recovered and the crystals of complex that was, the crystallization product of carboplatin 4.0, was collected; the purity of the product was detected by XRPD analysis, with the content of the carboplatin 4.0 in the product being up to 99% or more.

2. Preparation of Liquid Injection of Carboplatin 4.0

1) An appropriate amount of the above carboplatin 4.0 crystalline product (or reformulation) was ground into powder, followed by vacuum drying, and removing water of crystallization, and the carboplatin 4.0 powder was obtained;
2) 500 g of the above carboplatin 4.0 powder was dissolved in sterilized water, and quantified to 500 L to obtain an aqueous solution. The obtained aqueous solution was stirred and dissolved evenly at 45° C.±5° C., leaving it at room temperature for not less than 1 hour, so as to prepare a mother liquid, and then its content was tested;
3) if the content of above mother liquid met the standard by testing the mother liquid, the mother liquid was filtered and sterilized at room temperature and packaged into 5 mg/5 ml liquid injection, which was stored at 4° C. in the dark.

3. Comparative Example 1) the carboplatin and the 1,1-cyclobutanedicarboxylic acid with their respective purity of not less than 99% were mixed in a molar ratio of 1:1.1, so as to prepare a supersaturated aqueous solution; where such mixing and preparation operation was implemented at about 40° C. for about 4 hours to complete the reaction;
2) the reaction system was filtered, and the filtrate was kept at room temperature (20±5° C.) in the dark for 10 days, and the formation of crystals could be observed;
3) the solution was recovered, the crystalline product was collected, and the purity of the crystalline product was detected by XRPD analysis, with the content of carboplatin 4.0 in the product being less than 88%.

The following Examples 2-3 investigated the structure and physicochemical properties of carboplatin 4.0; unless otherwise specified, the carboplatin 4.0 bulk drug (i.e., the crystalline product of carboplatin 4.0) to be used was prepared according to the self-assembly process of Example 1. Additionally, the lyophilized powder obtained from carboplatin 4.0 bulk drug dissolved in water (hereinafter referred to as lyophilized powder a), the lyophilized powder obtained from carboplatin and 1,1-cyclobutanedicarboxylic acid that were physically mixed and dissolved in water (hereinafter referred to as lyophilized powder b) and the grinded powder obtained from physically mixed carboplatin and 1,1-cyclobutanedicarboxylic acid (hereinafter referred to as lyophilized powder c) were all prepared as follows:

1) 100 mg of carboplatin 4.0 bulk drug was weighed precisely, dissolved with 5.0 ml deionized water to obtain an aqueous solution; after standing at room temperature for 2 hours, the aqueous solution was frozen in a refrigerator at −70° C. for 4 hours, and then transferred to a lyophilizer (German Christ Lyophilizer Alpha2-4LD PLUS, where the temperature of cold trap is −69° C. and the vacuum is 10 pa) to lyophilize for 12 hours, and ground slightly in a mortar to obtain a white lyophilized powder, namely the lyophilized powder a;
2) a mixed sample containing 100 mg of carboplatin and 38 mg of 1,1-cyclobutanedicarboxylic acid (the molar ratio is about 1:1) was weighed precisely, and was prepared into lyophilized powder b according to the above preparation process of the lyophilized powder a;
3) 100 mg of carboplatin and 38 mg of 1,1-cyclobutanedicarboxylic acid were weighed precisely, mixed, and then ground slightly in a mortar to obtain a powder, namely the lyophilized powder c.

Example 2. Analysis of Structure and Physicochemical Properties of Carboplatin 4.0

1. $^{1}$HNMR Analysis

A certain amounts of 1,1-cyclobutanedicarboxylic acid and carboplatin were dissolved with 0.5 ml deuterated DMSO (DMSO-d6), so as to prepare a mixed test solution of 1,1-cyclobutanedicarboxylic acid and carboplatin. After standing for overnight, the mixed test solution was detected by $^{1}$HNMR.

Figure 2:
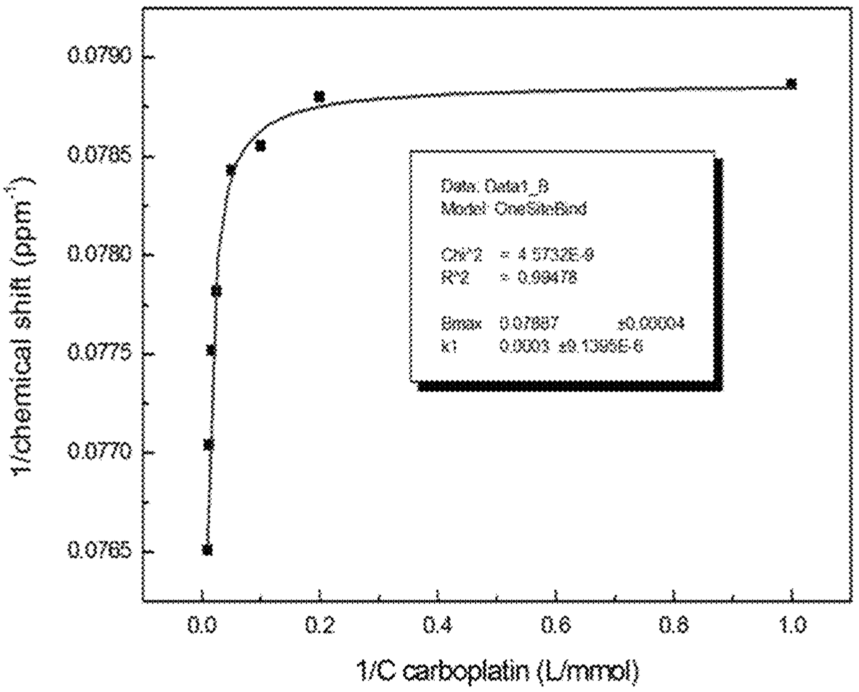
FIG. 2 is a nonlinear fitting diagram of the reciprocal of the chemical shift value of carboxyl hydrogen (1/Chemical shift) and the reciprocal of the molar concentration of carboplatin (1/C carboplatin)

According to the above method, 9 groups of the above mixed test solutions were prepared, numbered 0-8, concentrations of 1,1-cyclobutanedicarboxylic acid and carboplatin in each group of the mixed test solutions were shown in Table 1 (the addition amount of the 1,1-cyclobutanedicarboxylic acid was kept constant, and the addition amount of the carboplatin was changed), and $^{1}$H NMR analysis was implemented on the 9 groups of mixed test solutions respectively, and the results were shown in Table 1 and FIGS. 1 and 2.

The results showed that, except for two carboxyl hydrogen atoms in the 1,1-cyclobutanedicarboxylic acid molecule, the chemical shifts of all other hydrogen atoms did not change with the increase of the addition amount of carboplatin. The chemical shifts of the carboxyl hydrogen atoms of the 1,1-cyclobutanedicarboxylic acid changed significantly with the increase of the addition amount/concentration of the carboplatin (as shown in FIG. 1 and Table 1, where the relationship between the chemical shift of the carboxyl hydrogen atom and the concentration of the carboplatin may be roughly as follows: $y=12.69+0.00364x$), moving from a high field to a low field (12.681→43.422 ppm), which indicated that there was two hydrogen-bonds interaction between the 1,1-cyclobutanedicarboxylic acid and the carboplatin. In a process of titration, surprisingly, the chemical shift of the amino hydrogen ($NH_3$) in the carboplatin molecule did not change significantly, indicating that the amino hydrogen ($NH_3$) in the carboplatin molecule was little affected by the addition of the 1,1-cyclobutanedicarboxylic acid, in other words, the amino hydrogen ($NH_3$) in the carboplatin molecule did not form a hydrogen bond with the 1,1-cyclobutanedicarboxylic acid.

As shown in FIG. 2, the dissociation constant k1, which is 0.3 mmol/L, between carboplatin and 1,1-cyclobutanedicarboxylic acid was calculated by nonlinear fitting based on the chemical shift values of carboxyl hydrogen under different addition amounts of carboplatin. Based on the reciprocal of the chemical shift value of carboxyl hydrogen and the reciprocal of the molar concentration of carboplatin, the binding constant between 1,1-cyclobutanedicarboxylic acid and carboplatin was calculated to be $4.22\times10^{4}$ L/mol. This further indicated that there were indeed two hydrogen-bonds interaction between the two components of carboplatin 4.0 (i.e., carboplatin and 1,1-cyclobutanedicarboxylic acid), but the binding force between the two components is relatively weaker than the covalent bond.

TABLE 1

The addition amount of carboplatin and 1,1-cyclobutanedicarboxylic acid and the chemical shift of carboxyl hydrogen

| No. | 1,1-cyclobutane-dicarboxylic acid (mmol/L) | Carboplatin (mmol/L) | 1,1-cyclobutane-dicarboxylic acid: Carboplatin (Molar ratio) | chemical shift of carboxyl hydrogen (ppm) |
|---|---|---|---|---|
| 0 | 10 | 1 | 10:1 | 12.681 |
| 1 | 10 | 5 | 2:1 | 12.692 |
| 2 | 10 | 10 | 1:1 | 12.712 |
| 3 | 10 | 20 | 1:2 | 12.751 |
| 4 | 10 | 40 | 1:4 | 12.842 |
| 5 | 10 | 60 | 1:6 | 12.911 |
| 6 | 10 | 80 | 1:8 | 12.992 |
| 7 | 10 | 100 | 1:10 | 13.071 |
| 8 | 10 | 200 | 1:20 | 13.422 |

2. DSC Analysis Test

Figure 3:
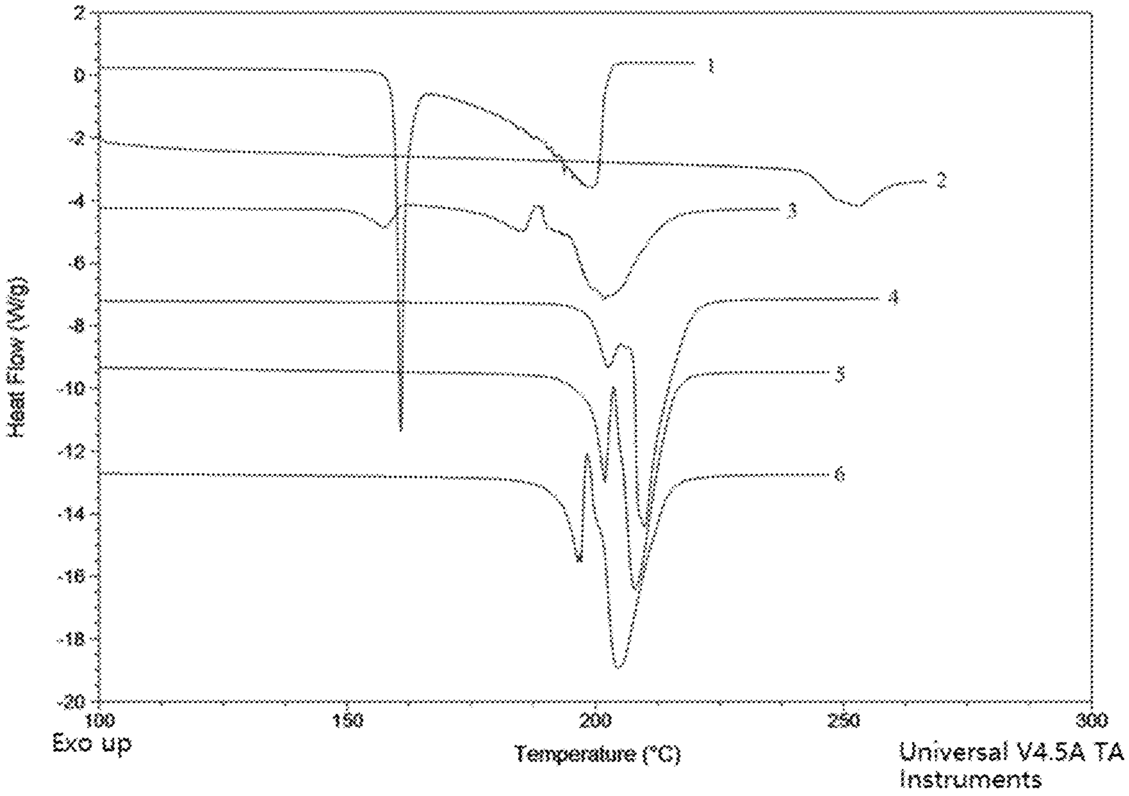

1) DSC Analysis (1) An appropriate amount of carboplatin 4.0 bulk drug, lyophilized powder a, lyophilized powder b, mixed powder c, carboplatin, and 1,1-cyclobutanedicarboxylic acid were weighed precisely, and measured for their thermogravimetric parameters (i.e., a melting process) with a DSC analyzer, and the results were shown in FIG. 3.

The results showed that DSC curves of three samples, which were the Carboplatin 4.0 bulk drug (Curve 5 in FIG. 3), the lyophilized powder a (Curve 4 in FIG. 3) and the lyophilized powder b (Curve 6 in FIG. 3), were relatively similar, where their endothermic peaks began to appear at 198.94° C., 198.68° C. and 193.06° C., respectively. Relatively speaking, the endothermic process (or curve) of the lyophilized powder a was closer to that of the carboplatin 4.0 bulk drug, while the endothermic process of the lyophilized powder b was slightly different from that of the carboplatin 4.0 bulk drug. In addition to an endothermic peak at 198° C., the mixed powder c also had an obvious endothermic peak at 153.05° C. (see Curve 3 in FIG. 3), and this peak was close to the endothermic peak of 1,1-cyclobutanedicarboxylic acid (see Curve 1 in FIG. 3), and it can be confirmed that this peak was the endothermic peak of 1,1-cyclobutanedicarboxylic acid. It could be seen that the physical mixture of carboplatin and 1,1-cyclobutanedicarboxylic acid exhibited the characteristics of its composition. Carboplatin did not show any endothermic peak around 153° C. and 198° C., and had a decomposition peak when the temperature increased to 252° C. (see Curve 2 in FIG. 3).

Figure 14:
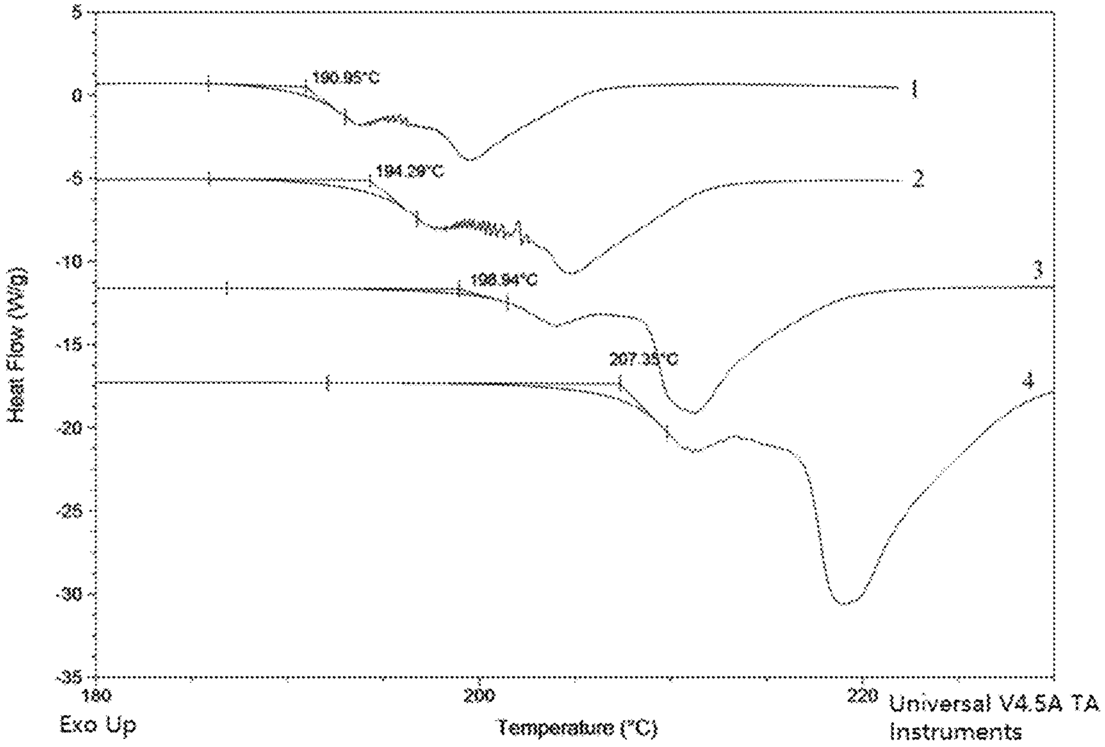
FIG. 14 is a DSC measurement diagram of carboplatin 4.0 bulk drug under different heating rate conditions.

(2) In order to verify whether the peak around 198° C. was a melting peak of carboplatin 4.0, the melting point of carboplatin 4.0 was further checked by changing the heating rate, and the results were shown in FIG. 14. In this case, the heating rates corresponding to Curves 1-4 in FIG. 14 were: 3° C./min, 5° C./min, 10° C./min, and 20° C./min, respectively.

As shown in FIG. 14, with the increase of the heating rate, the melting peak shifts to the right, thus it can be determined that the carboplatin 4.0 has no constant melting point, and the peak displayed by DSC is a melting decomposition peak.

Figure 4:
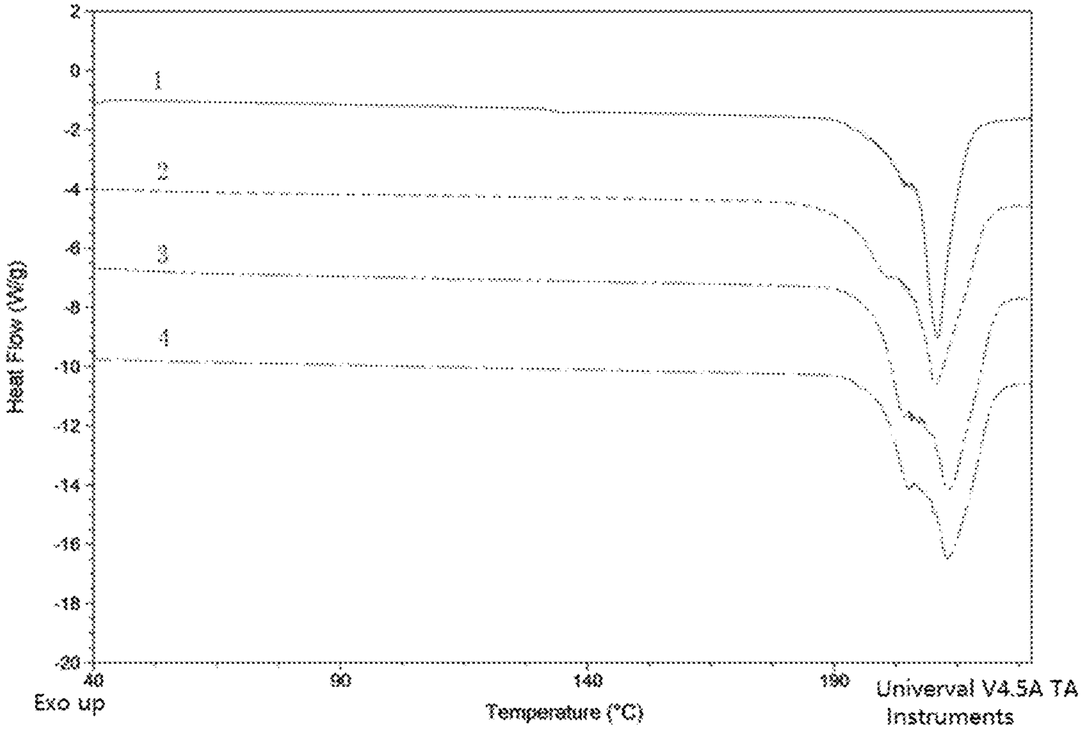
FIG. 4 is a DSC measurement diagram of four batches of carboplatin 4.0 bulk drug.

(3) 4 batches of carboplatin 4.0 bulk drug were prepared, numbered 1-4; an appropriate amount of each of 1-4 batches of carboplatin 4.0 bulk drug was taken, their thermogravimetric parameters were measured with a DSC analyzer, and the results were shown in FIG. 4. As can be seen, 4 different batches of the carboplatin 4.0 bulk drug also all showed endothermic peaks around 198° C. only, and no endothermic peak appeared around 153° C. and 252° C.

2) Result and Discussion (1) The DSC curves of the carboplatin 4.0, the lyophilized powder a and the mixed powder c showed great differences, where not only the position and peak shape of the thermal absorption peak (or endothermic peak) showed significant changes, but also the number of absorption peaks was different;

(2) the carboplatin 4.0 bulk drug and the lyophilized powder a began to show a sharp phase transition peak around 198° C., while the lyophilized powder b had a phase transition peak near 193° C., indicating that the two components of the carboplatin 4.0 (carboplatin and 1,1-cyclobutanedicarboxylic acid) were in a crystalline state, while the two components of the lyophilized powder b were in a semi-crystalline or amorphous state.

(3) There were differences between the lyophilized powder b and the mixed powder c, while the DSC curve of the lyophilized powder b was similar to that of the carboplatin 4.0 and there was no dissolution endothermic peak of the 1,1-cyclobutanedicarboxylic acid dissolution around 153° C., indicating that, after water dissolution and lyophilization, carboplatin and 1,1-cyclobutanedicarboxylic acid formed an analogue of carboplatin 4.0 due to hydrogen bonding force, however, its crystalline state was significantly different from the carboplatin 4.0 assembled and prepared by the special process of this example.

(4) Comparing the DSC curves of the carboplatin 4.0 bulk drug and the lyophilized powder a, it can be seen that the DSC curves of the two were relatively similar; after the carboplatin 4.0 was lyophilized into the lyophilized powder a, its absorption peak shifted slightly, but there was no endothermic peak around 153° C., indicating that the lyophilization process had little effect on the binding between the two components of the carboplatin 4.0.

The above DSC test results show that the carboplatin 4.0 bulk drug (solid state) is indeed significantly different from the physical mixture (such as the above lyophilized powder b and mixed powder c) of the carboplatin and the 1,1-cyclobutanedicarboxylic acid, since the carboplatin 4.0 is formed from two components by hydrogen bonding, and is not a simple physical mixture. This further illustrates that, through the self-assembly process of the present disclosure, the two components carboplatin and 1,1-cyclobutanedicarboxylic acid indeed form a new chemical entity (i.e., carboplatin 4.0) due to hydrogen bonding force, which can exist stably under milder conditions.

3. XRPD Analysis Test

Figure 5:
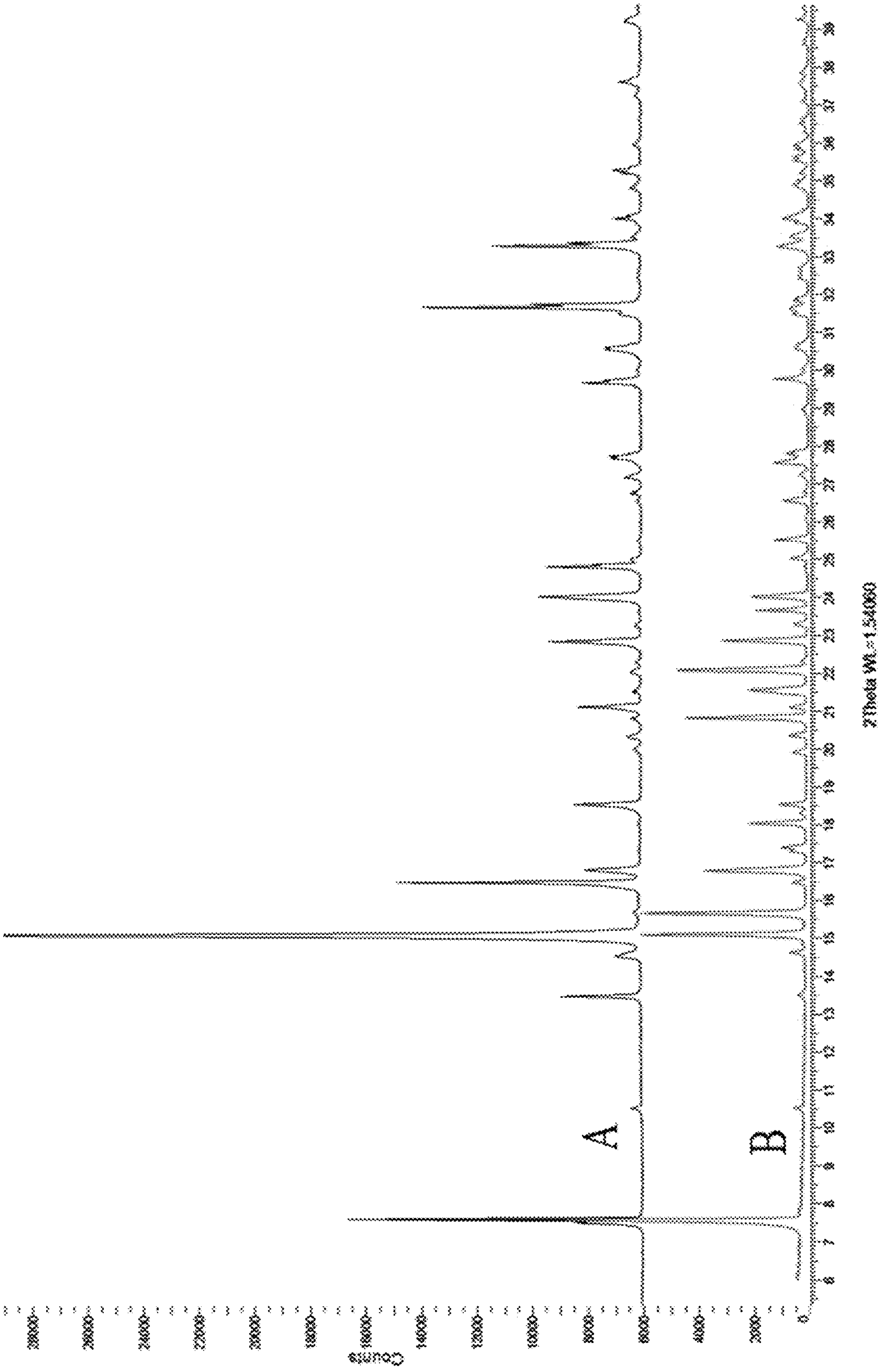
FIG. 5 is an XRPD diagram of carboplatin 4.0 bulk drug, where A is an XRPD diagram measured by a reflection method, and B is an XRPD diagram measured by a transmission method.

This test found that since carboplatin 4.0 bulk drug was needle-like crystal and there was a serious preferential orientation, the use of a conventional reflection method cannot accurately reflect the structural information of a sample, while the use of a transmission method weakened the preferential orientation, which can reflect the structural information of the sample more realistically and be more accurate for quantitative analysis (the transmission and reflection results of carboplatin 4.0 bulk drug were shown in FIG. 5). Therefore, in the following experiments, the transmission method was used for XRPD analysis.

Figure 6:
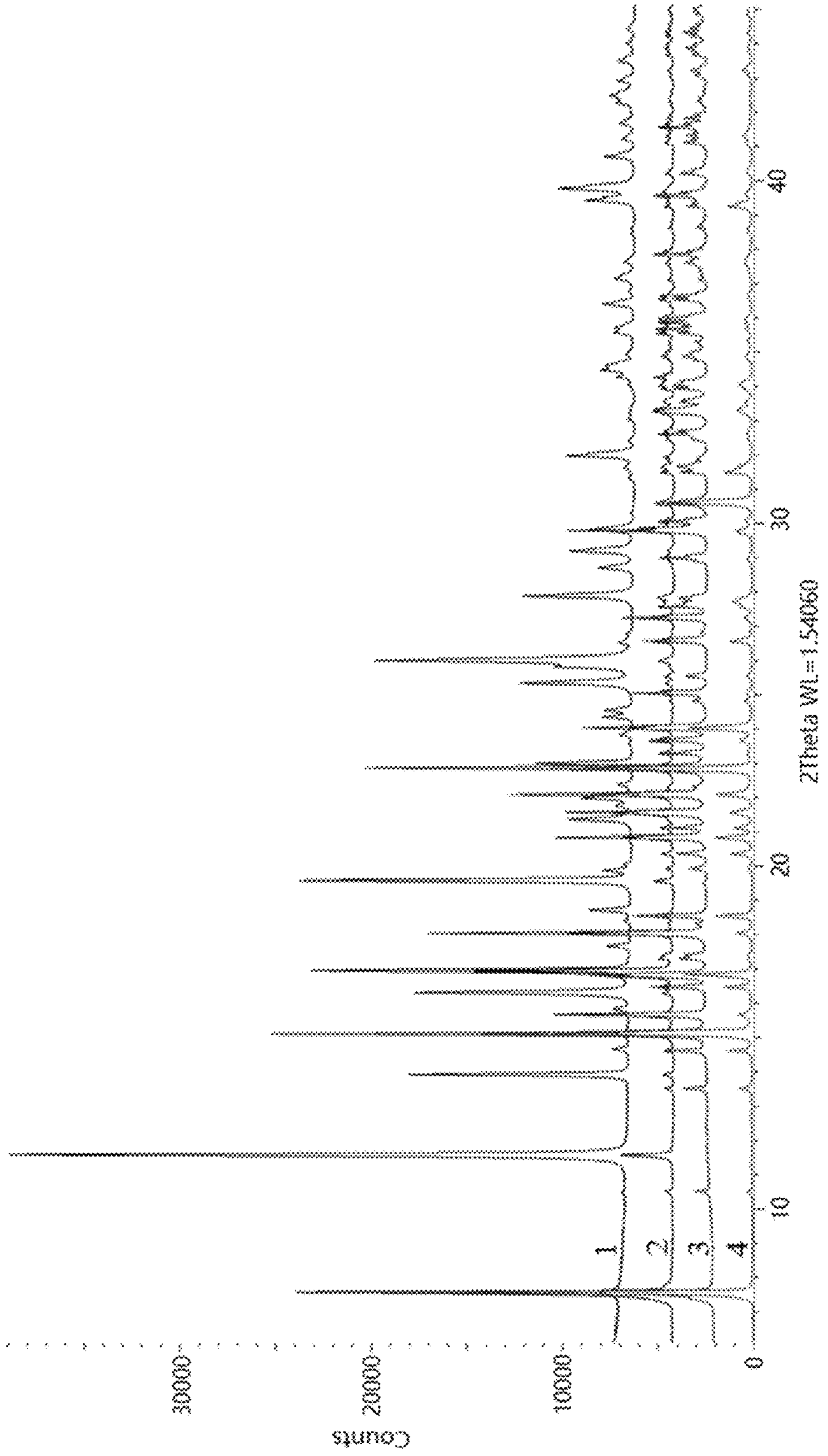
Figure 7:
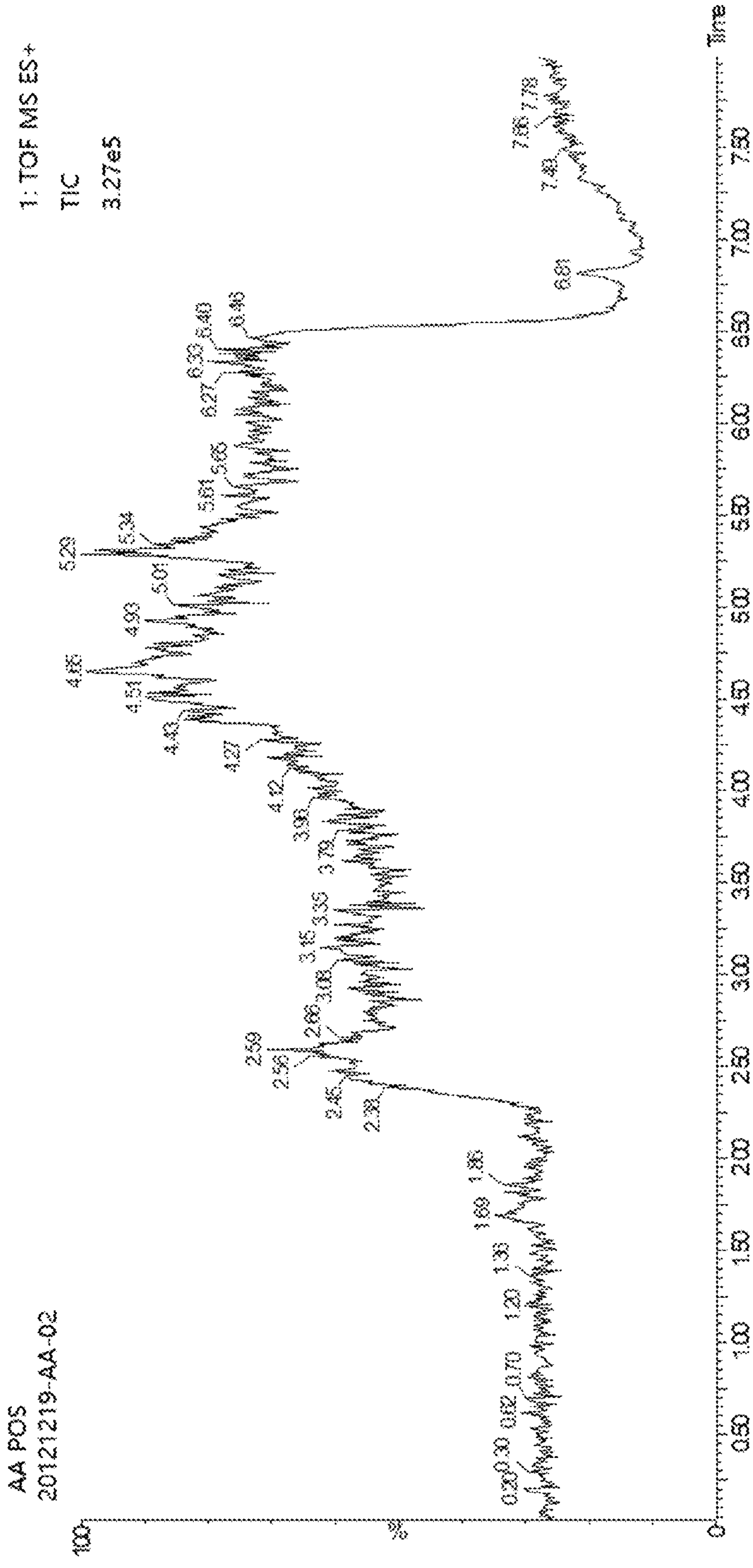
FIG. 7 is a spectrogram of LC-MS analysis for carboplatin 4.0, where
Figure 8:
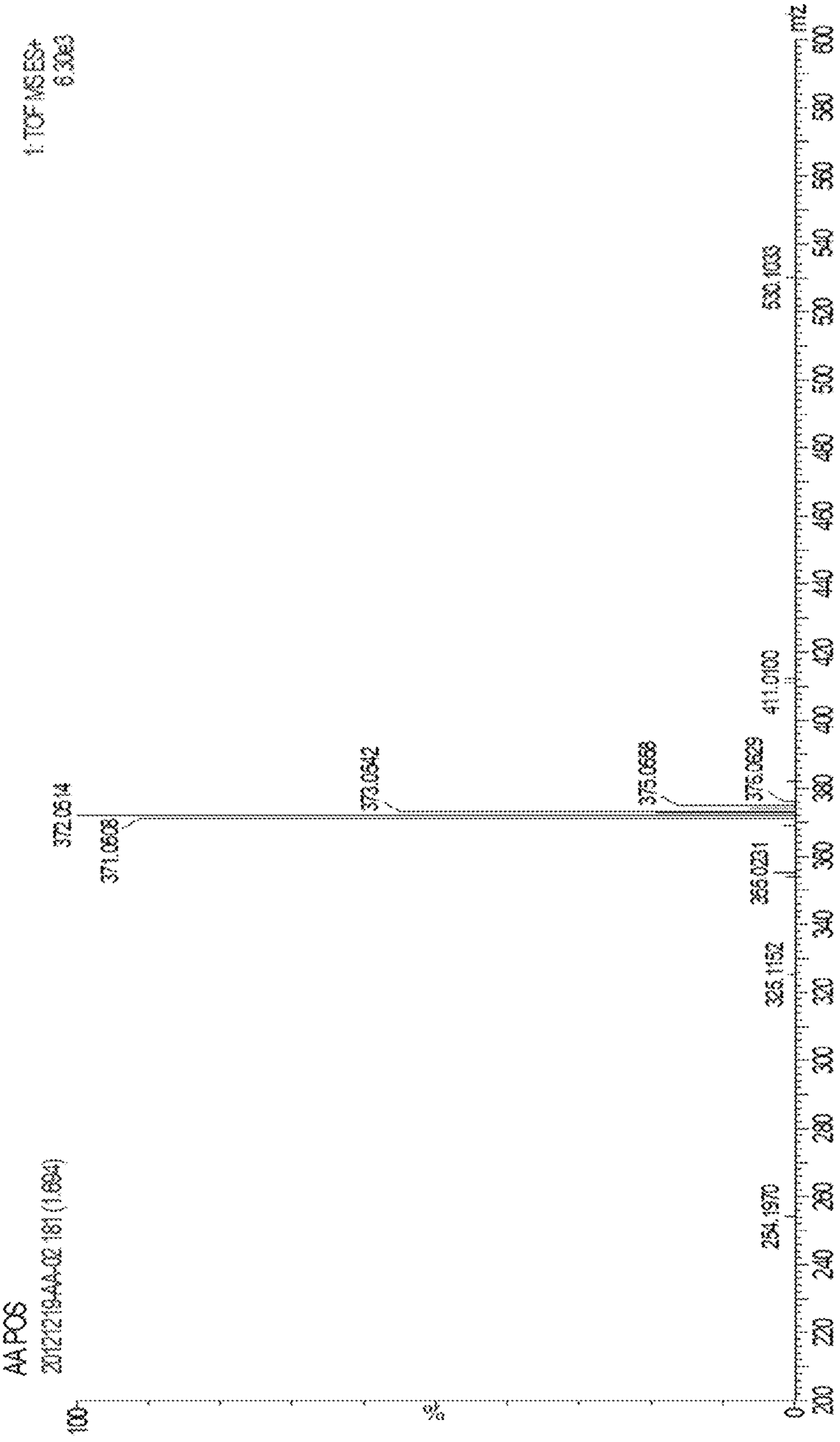
FIG. 8 is a spectrogram of LC-MS analysis for carboplatin 4.0, where FIG. 8 are is the mass spectrogram of total ion currents of carboplatin in a positive ion mode (retention time RT=0.83 min)
Figure 9:
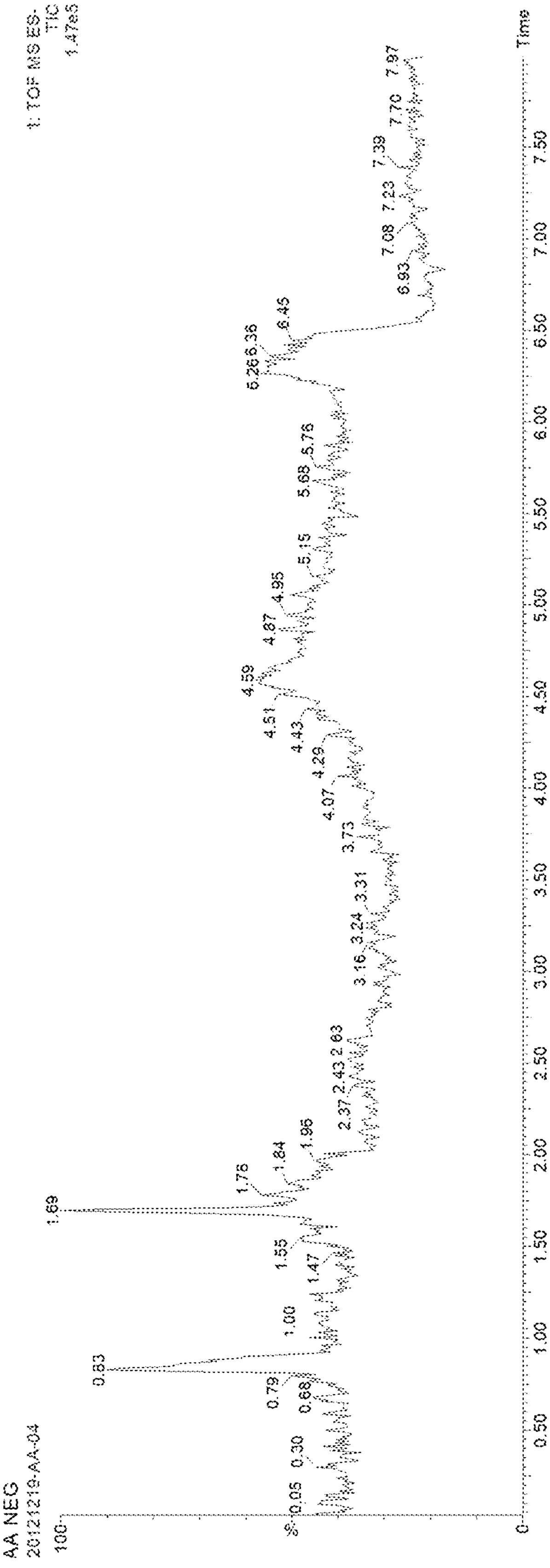
FIG. 9 is the chromatogram of total ion currents of 1,1-cyclobutanedicarboxylic acid in a negative ion mode, (retention time RT=1.7 min)
Figure 10:
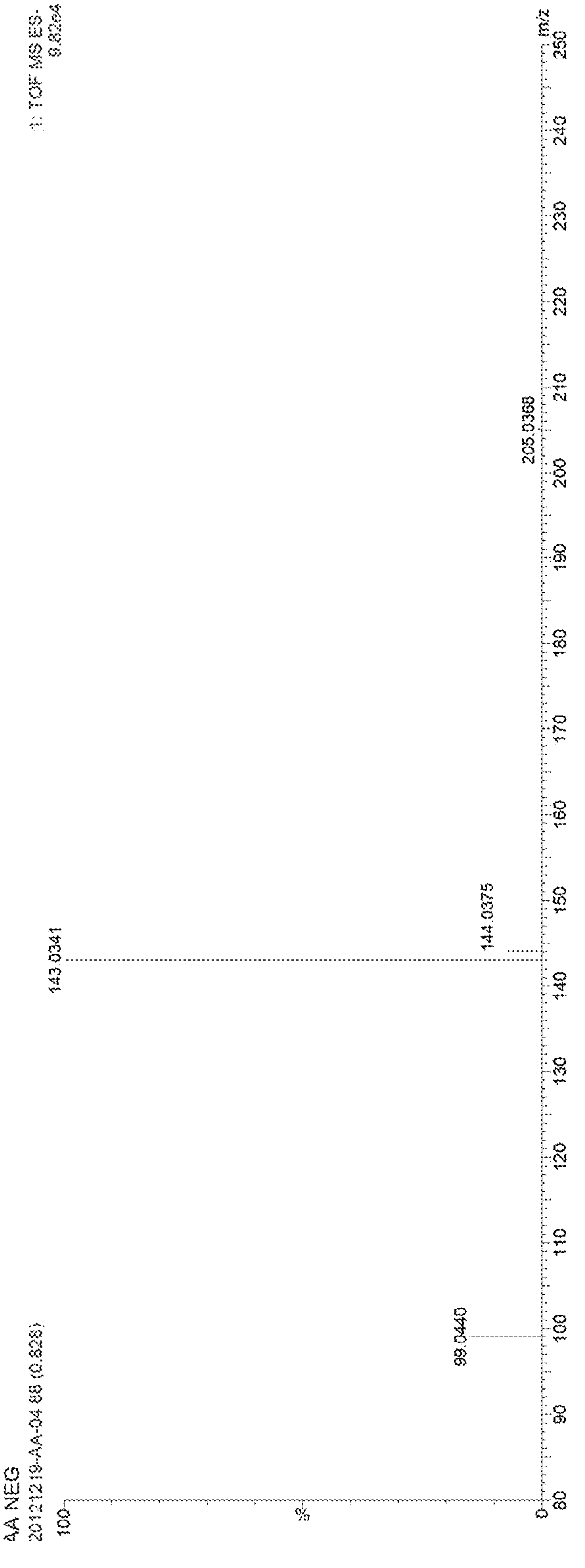
FIG. 10 is the mass spectrogram of total ion currents of 1,1-cyclobutanedicarboxylic acid in a negative ion mode, (retention time RT=1.7 min)

XRPD Analysis:

100 mg of the carboplatin 4.0 bulk drug, the lyophilized powder a, the lyophilized powder b, the mixed powder c, the carboplatin, and the 1,1-cyclobutanedicarboxylic acid samples were loaded into a transmission sample holder, respectively, the same experimental conditions were used for XRPD determination, and the results were shown in FIG. 6.

The results showed that there were significant differences among the XRPD spectrums of the carboplatin 4.0 bulk drug (Spectrum 4 in FIG. 6), the lyophilized powder a (Spectrum 3 in FIG. 6), the lyophilized powder b (Spectrum 2 in FIG. 6), and the mixed powder c (Spectrum 1 in FIG. 6), as follows:

(1) Both the lyophilized powder b and the mixed powder c had diffraction peaks at 2θ of about 11.55±0.2°, which were characteristic peaks of carboplatin; and, the XRPD spectrums of the carboplatin 4.0 bulk drug and the lyophilized powder a were similar, and their main characteristic peaks were at positions where 2θ was about 7.55°, 10.51°, 14.63°, 15.10°, 15.66°, 16.78°, 18.55°, 20.83°, 22.86°, 23.67°, 24.02°, etc., but they had no diffraction peak at 2θ of about 11.55±0.2°. This demonstrated that the carboplatin 4.0 bulk drug and the lyophilized powder a were different from the physical mixture of the carboplatin and the 1,1-cyclobutanedicarboxylic acid (i.e., the lyophilized powder b and the mixed powder c), further indicating that, through the self-assembly process of the present disclosure, the two components carboplatin and 1,1-cyclobutanedicarboxylic acid indeed formed a new chemical entity (i.e., carboplatin 4.0) due to hydrogen bonding force, which can exist stably under milder conditions.

Combined with the above comparative analysis, it is indicated that the characteristic diffraction peak at about 11.55±0.2° can be used as the quality control peak of carboplatin 4.0. In other words, the XRPD analysis method can be used as a quality control method for the purity of carboplatin 4.0 bulk drug, and can be further used as a determination method for the content of carboplatin 4.0 in carboplatin 4.0 bulk drug.

4. LC-MS Analysis Test

1) LC-MS Analysis

LC-MS analysis was performed on the crystalline product of carboplatin 4.0 in this example according to the conventional operation method.

LC-MS analysis was performed on the carboplatin 4.0, and the dissociated carboplatin and 1,1-cyclobutanedicarboxylic acid were detected in a positive ion mode and a negative ion mode, respectively (see FIG. 7-FIG. 10), where the molecular ion peak of carboplatin $[M+H]^+$ was at m/z 372.0514, and the molecular ion peak of 1,1-cyclobutanedicarboxylic acid $[M+H]^-$ was at m/z 143.0341, indicating that carboplatin 4.0 was dissociated into carboplatin and 1,1-cyclobutanedicarboxylic acid under liquid chromatography separation conditions.

2) Flow-Injection Mass Spectrometry

Figure 11:
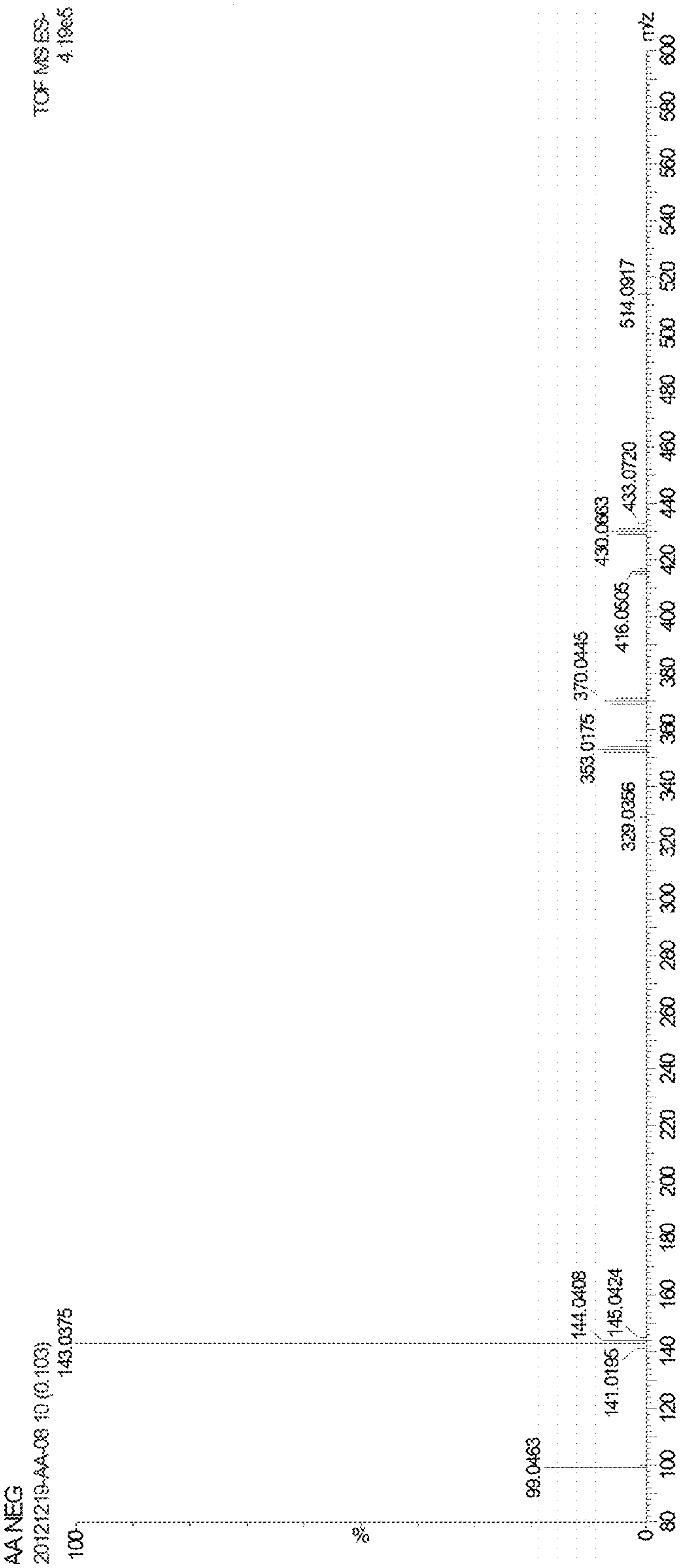
FIG. 11 is a mass spectrogram of the carboplatin 4.0 sample in a negative ion mode.
Figure 12:
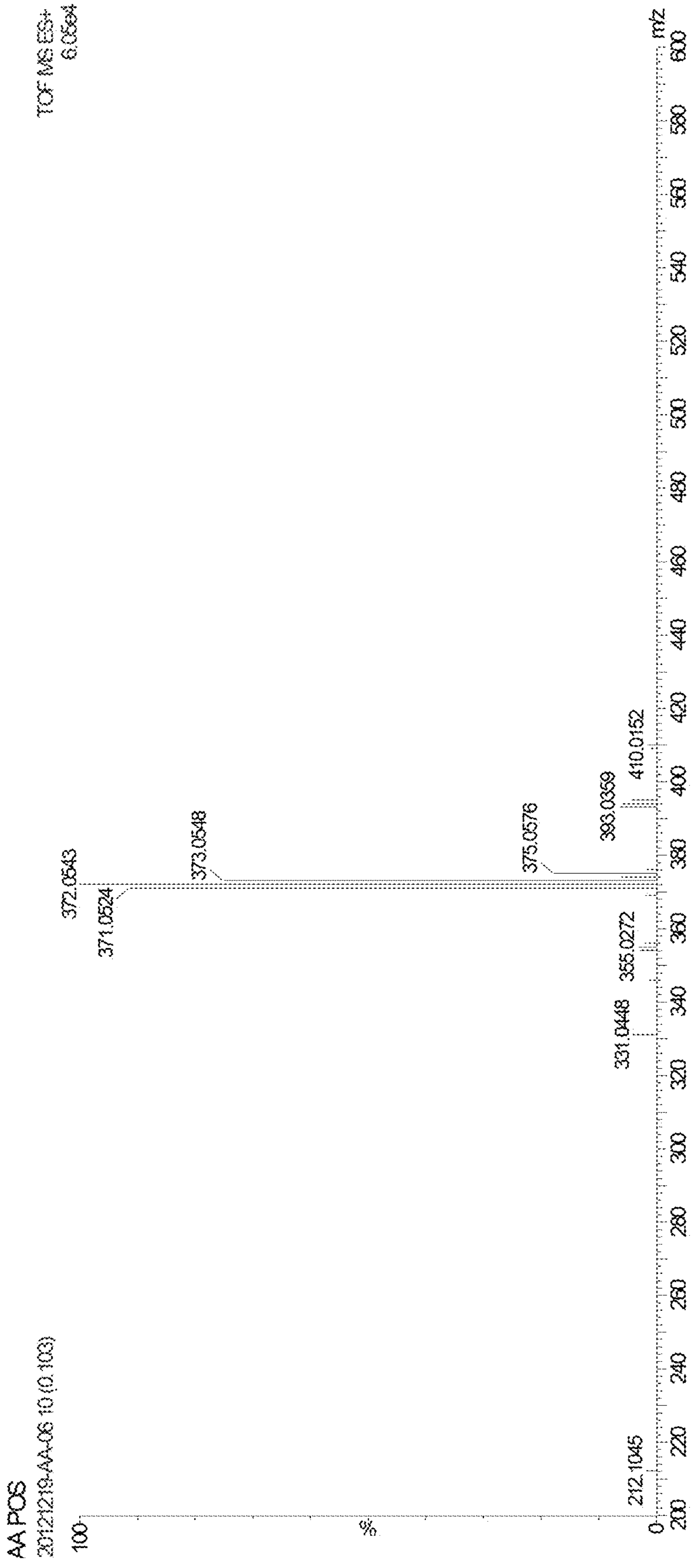
FIG. 12 is a mass spectrogram of the carboplatin 4.0 sample in a positive ion mode.

Considering that the liquid chromatography separation would break the intramolecular hydrogen bonds of carboplatin 4.0, flow injection was used for sample introduction, so as to analyze the carboplatin 4.0 aqueous solution directly. The molecular ion peaks of carboplatin 4.0 [m/z 514.0917] and 1,1-cyclobutanedicarboxylic acid [m/z 143.0375] were observed in the negative ion mode (see FIG. 11), and only the molecular ion peak of carboplatin [m/z 372.0543] was detected in the positive ion mode (see FIG. 12).

3) The above flow-injection mass spectrometry was performed on the physical mixed sample of carboplatin and 1,1-cyclobutanedicarboxylic acid (molar ratio of 1:1), and it was found that the same ions as carboplatin 4.0 were also generated in the negative ion mode.

The above analysis results showed that the chromatographic separation would destroy hydrogen bonds in the carboplatin 4.0, so the liquid chromatography-mass spectrometry method was not suitable for the quality standard study of carboplatin 4.0. The use of flow injection for sample introduction can perform the mass spectrometry directly, and can obtain the accurate molecular weight of carboplatin 4.0 in the negative ion mode. However, since the physical mixed sample of carboplatin and 1,1-cyclobutanedicarboxylic acid also produced the same ions as carboplatin 4.0 in this mode, the mass spectrometry cannot distinguish carboplatin 4.0 from the physical mixture of carboplatin and 1,1-cyclobutanedicarboxylic acid, but only be used for accurate determination of the molecular weight of carboplatin 4.0.

Example 3. Helicase Validation Method

In this experiment, the effect of a helicase on carboplatin 4.0 was verified by a DNA binding test involved by the helicase, including: using the supercoiled and linear plasmid DNA (Hr. pcDNA, which can be extracted in a conventional manner) as a template, changing the DNA conformation through reactions by combining with different platinum-based anticancer drugs, and then distinguishing different platinum drugs by differences in gel electrophoretograms.

Figure 13:
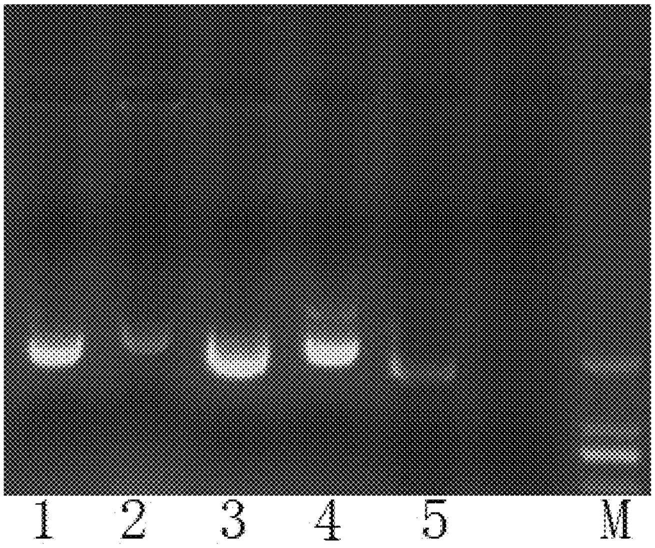
FIG. 13 is an electrophoregram of the DNA binding experiments of carboplatin 4.0 and carboplatin with the participation of helicase.

The binding of platinum drugs with the plasmid DNA was affected by many factors, such as a drug concentration (concentration of carboplatin or carboplatin 4.0), a reaction time, plasmid size, Cl ion in solution, EDTA, acidity and alkalinity (pH), temperature, etc., the inventors conducted a large number of comparative experiments and finally selected the following conditions, including the drug concentration of 0.05-0.2 mmol/L, the plasmid size of about 6000 bp, the reaction time of 1 hour, the pH of 6.5-7.3, the buffer without EDTA and Cl ions, and the temperature of 37° C., under which there were significant differences in DNA binding of carboplatin and carboplatin 4.0 (see FIG. 13).

Details were as follows:

In this experiment, T4 GP41 DNA helicase (hereinafter referred to as T4) was used, which was imported from iCloning Biotech Co., Ltd.

Experimental conditions: 0.8% agarose (imported package from Promega company) gel electrophoresis, pH 6.5-7.3, 37° C., the reaction time was 1 hour, and the drug concentration was 0.1 mmol/L; 5 V 1 Hr. pcDNA: 6000 bp, 1 mmol/L ATP (imported package from Promega company) added.

The following samples (test numbers 1-5 and M) were analyzed under the above experimental conditions, and the addition of pcDNA, drugs, and helicases in each sample was shown as follows:

Test 1: pcDNA+Carboplatin+T4

Test 2: pcDNA+Carboplatin 4.0+T4

Test 3: pcDNA+Carboplatin 4.0

Test 4: pcDNA+Carboplatin

Test 5: pcDNA

Test M: Marker (Reference Standard)

The test results were shown in FIG. 13, where the numbers 1-5 and M in FIG. 13 corresponded to the above test numbers respectively.

The results showed that the electrophoresis situations of the plasmids in Test 1 and Test 4 were roughly the same, indicating that the helicase had no obvious effect on the carboplatin; but carboplatin 4.0 was quite different, the electrophoresis situations of the plasmids in Test 3 and Test 5 were basically the same, indicating that carboplatin 4.0 itself was basically not bound with the supercoiled plasmid (pcDNA); and, the electrophoresis speed of the plasmid in Test 2 was the slowest, indicating that the helicase disrupted the hydrogen bond of the carboplatin 4.0 and released the carboplatin, and the released carboplatin was combined with the plasmid to form a DNA adduct, which reduced the electrophoresis speed.

What is claimed is:

1. A preparation method of a carboplatin complex, wherein the carboplatin complex is a complex formed by combining carboplatin and 1,1-cyclobutanedicarboxylic acid through two hydrogen bonds, each of the two hydrogen bonds being formed between a carbonyl oxygen of a carboplatin molecule and a carboxyl hydrogen of a 1,1-cyclobutanedicarboxylic acid molecule, and the preparation method comprises:

mixing the carboplatin and the 1,1-cyclobutanedicarboxylic acid in a molar ratio of 1:1.5-3 at 65° C.±10° C. for not less than 0.5 hours, so as to prepare a supersaturated aqueous solution; and collecting crystals of the carboplatin complex.

2. A preparation method of a pharmaceutical preparation comprising the carboplatin complex prepared by the preparation method according to claim 1 as an active component, comprising:

preparing the crystals of the carboplatin complex according to the preparation method of claim 1, and grinding and drying, so as to obtain a powder of the carboplatin complex; and preparing the powder of the carboplatin complex into a preparation.

3. The preparation method according to claim 2, further comprising:

dissolving the powder of the carboplatin complex in sterilized water, stirring and dissolving at 45° C.±5° C., and standing at room temperature for 1 hour or more, so as to obtain a mother liquid;

filtering and sterilizing the mother liquid at room temperature and then packaging into a liquid injection; or preparing the mother liquid into a lyophilized powder injection, an oral solid preparation, a gel preparation, or a spray preparation.

4. The preparation method according to claim 1, wherein a structure of the carboplatin complex is:

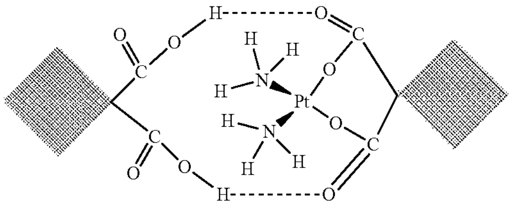

.

* * * * *